United States Patent [19]

Heeres et al.

[11] Patent Number: 4,490,540

[45] Date of Patent: Dec. 25, 1984

[54] (2-ARYL-4-PHENYLTHIOALKYL-1,3-DIOX-OLAN-2-YLMETHYL)AZOLE DERIVATIVES

[75] Inventors: Jan Heeres; Louis J. E. Van der Veken, both of Vosselaar, Belgium

[73] Assignee: Janssen Pharmaceutica N.V., Beerse, Belgium

[21] Appl. No.: 487,600

[22] Filed: Apr. 29, 1983

Related U.S. Application Data

[63] Continuation of Ser. No. 301,672, Sep. 14, 1981, abandoned, which is a continuation-in-part of Ser. No. 209,790, Nov. 24, 1980, abandoned.

[51] Int. Cl.$^3$ ............................................ C07D 403/06
[52] U.S. Cl. ................................. 548/336; 548/262; 424/273 R; 424/269
[58] Field of Search ............................... 548/336, 262; 424/273 R, 269

[56] References Cited

U.S. PATENT DOCUMENTS

| 3,936,470 | 2/1976 | Heeres | 548/336 |
| 4,101,664 | 7/1978 | Heeres | 548/336 |
| 4,101,665 | 7/1978 | Heeres | 548/336 |
| 4,120,869 | 10/1978 | Heeres | 548/336 |
| 4,144,346 | 3/1979 | Heeres et al. | 548/336 |

Primary Examiner—Jane T. Fan
Attorney, Agent, or Firm—Geoffrey G. Dellenbaugh

[57] ABSTRACT

The present invention relates to a series of (2-aryl-4-phenylthioalkyl-1,3-dioxolan-2-ylmethyl)azole derivatives which are useful as antifungal and antineoplastic agents.

12 Claims, No Drawings

(2-ARYL-4-PHENYLTHIOALKYL-1,3-DIOXOLAN-2-YLMETHYL)AZOLE DERIVATIVES

CROSS-REFERENCE TO RELATED APPLICATIONS

This application is a continuation of application Ser. No. 301,672, filed 9/14/81, now abandoned, which is a continuation-in-part of our copending application Ser. No. 209,790, filed Nov. 24, 1980, now abandoned.

BACKGROUND OF THE INVENTION

In U.S. Pat. Nos. 3,936,470; 4,101,664; 4,101,665; 4,120,869; and 4,144,346, and in U.S. application Ser. No. 53,640, filed June 29, 1979, there are described a number of (2-aryl-4-arylthiomethyl-1,3-dioxolan-2-ylmethyl)-1H-imidazoles and (2-aryl-4-aryloxymethyl-1,3-dioxolan-2-ylmethyl)-1H-imidazoles and 1H-1,2,4-triazoles, said compounds displaying pharmaceutically interesting properties as antifungal agents. The compounds of the present invention differ therefrom by their pharmacological properties and either by the replacement of the aryloxymethyl group by a phenylthiomethyl group or a homolog thereof or by the nature of the substituents on said phenyl group.

DESCRIPTION OF THE PREFERRED EMBODIMENTS

This invention is concerned with novel (2-aryl-4-phenylthioalkyl-1,3-dioxolan-2-ylmethyl)-1H-imidazoles and 1H-1,2,4-triazoles which may be represented by the formula:

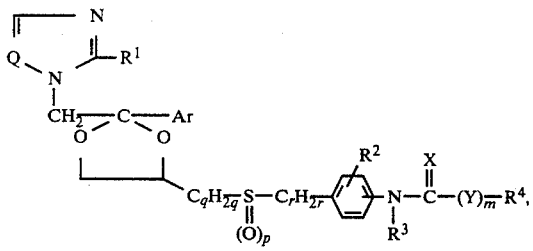

the pharmaceutically acceptable acid addition salts and the stereochemically isomeric forms thereof, wherein Q is a member selected from the group consisting of CH and N;

$R^1$ is a member selected from the group consisting of hydrogen and lower alkyl;

Ar is aryl;

p is 0 or the integer 1 or 2;

q is the integer 1,2 or 3;

r is 0 or the integer 1 or 2;

$R^2$ is a member selected from the group consisting of hydrogen, lower alkyl, lower alkyloxy and halo;

$R^3$ is a member selected from the group consisting of hydrogen, lower alkyl and aryllower alkyl;

X is a member selected from the group consisting of O and S;

Y is a member selected from the group consisting of O, S and $NR^5$, wherein $R^5$ is a member selected from the group consisting of hydrogen and lower alkyl;

m is 0 or the integer 1; and $R^4$ is a member selected from the group consisting of hydrogen, alkyl, mono-, di- and trihalolower alkyl, lower alkenyl, lower alkynyl, cycloalkyl, hydroxylower alkyl, lower alkyloxylower alkyl, aryloxylower alkyl, aryllower alkyloxylower alkyl, mei alkyl, lower alkylthiolower alkyl, arylthiolo aryllower alkylthiolower alkyl, lower bonyloxylower alkyl, arylcarbonyloxylower alk lower alkylcarbonyloxylower alkyl, aryl, ary alkyl, lower alkyloxycarbonyllower alkyl, amino mono- and di(lower alkyl)amino; provided that Y radical $NR^5$ when m is 1 and $R^4$ is hydrogen, amino mono- or di(lower alkyl)amino;

wherein aryl is a phenyl group which is optionally substituted with 1 to 3 substituents each independently selected from the group consisting of halo, lower alkyl, lower alkyloxy and nitro.

In the foregoing and the following definitions the term halo is generic to fluoro, chloro, bromo and iodo; the term "lower alkyl" is meant to include straight and branched hydrocarbon radicals having from 1 to 6 carbon atoms such as, for example, methyl, ethyl, 1-methylethyl, 1,1-dimethylethyl, propyl, butyl, pentyl, hexyl and the like; "alkyl" is meant to include the above mentioned meaning of "lower alkyl" and the higher homologs having from 7 to 10 carbon atoms such as, for example, heptyl, octyl, nonyl, decyl and the like; "lower alkenyl" and "lower alkynyl" denote straight and branched alkenyl, respectively alkynyl, radicals having from 2 to 6 carbon atoms, such as, for example, ethenyl, 2-propenyl, 2-butenyl and the like, and, respectively, ethynyl, 2-propynyl, 2-butynyl and the like; and "cycloalkyl" is meant to include cyclopropyl, cyclobutyl, cyclopentyl and cyclohexyl.

Preferred compounds within the present invention are those wherein $R^1$ is hydrogen.

Particularly preferred compounds are those wherein $R^1$ is hydrogen and Q is CH.

More particularly preferred compounds are those wherein $R^1$ is hydrogen, Q is CH and r is 0.

Especially preferred compounds within the scope of the invention are those wherein $R^1$ is hydrogen, Q is CH, r is 0 and the

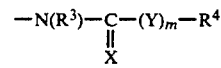

group is attached to the 4-position of the phenyl ring.

The most preferred compounds within the scope of the invention are ethyl cis-[4-[2-(2,4-dichlorophenyl)-2-(1H-imidazol-1-ylmethyl)-1,3-dioxolan-4-ylmethylthio]phenyl]carbamates.

In order to simplify the structural representation of the compounds of formula (I) and of certain starting materials and intermediates used in the preparation thereof, the 2-aryl-2-(1H-imidazol-1-ylmethyl or 1H-1,2,4-triazol-1-ylmethyl)-1,3-dioxolan-4-yl group, wherein Ar, Q and $R^1$ have the previously indicated meaning, may be represented by the symbol D throughout the following specification.

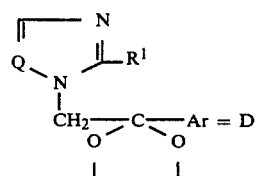

The compounds of formula (I) can generally be prepared by reacting a dioxolane of formula (II) with an appropriately substituted azole of formula (III).

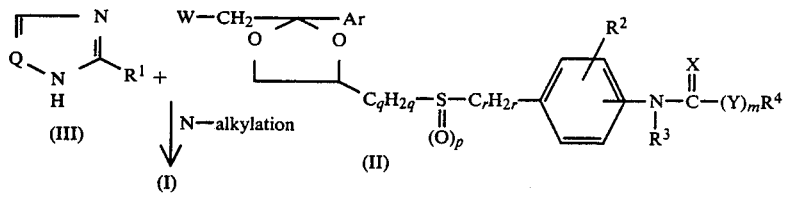

In the reactants of formula (II) and (III) Q, $R^1$, Ar, q, p, r, $R^2$, $R^3$, X, Y, m and $R^4$ are as previously described and W is a reactive leaving group such as, for example, halo, preferably chloro, bromo or iodo, or a sulfonyloxy group, e.g., methylsulfonyloxy, 4-methylphenylsulfonyloxy and the like.

The above described N-alkylation reaction can generally be carried out by stirring the reactants together in the presence of a relatively polar reaction-inert solvent such as, for example, N,N-dimethylformamide, N,N-dimethylacetamide, dimethyl sulfoxide, hexamethylphosphortriamide, acetonitrile, 1,4-dioxane, benzonitrile, 2-propanone and the like or mixtures thereof. Such solvents can also be used in combination with other reaction-inert solvents such as, for example, aliphatic-, alicyclic- and aromatic hydrocarbons, e.g., hexane, cyclohexane, benzene, methylbenzene, petroleumether and the like. Elevated temperatures of from about 30° to about 220° C., preferably from about 80° to about 170° C. are appropriate and, most conveniently, the reaction is carried out at the reflux temperature of the reaction mixture. In order to enhance the reaction rate it may be advantageous to carry out the reaction in the presence of an appropriate base or to carry out the reaction starting from an alkali metal salt of an appropriately substituted azole of formula (III). Suitable bases which may be used include alkali metal oxides, hydroxides, carbonates and hydrogen carbonates as well as amines such as N,N-diethylethanamine, pyridine and the like.

The compounds of formula (I) wherein p is 0, said compounds being represented by the formula (I-a), can also be prepared by the reaction of an appropriate reactive ester of formula (IV) with an appropriately substituted benzenethiol of formula (V).

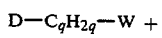

(IV)

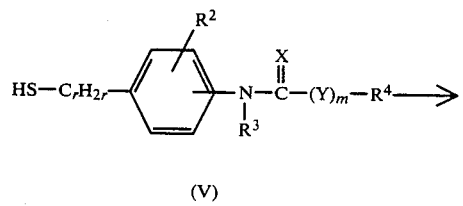

(V)

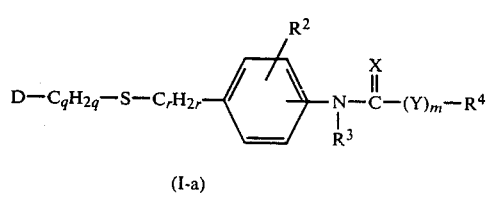

(I-a)

In the formulae (IV) and (V) D, W, q, r, $R^2$, $R^3$, X, Y, m and $R^4$ are as previously described.

The reaction of (IV) with (V) can be carried out following standard S-alkylating procedures, e.g., by stirring the reactants together at somewhat elevated temperatures and in the presence of an appropriate base. Preferably the reaction is carried out in a suitable reaction-inert solvent such as, for example, 4-methyl-2-pentanone, 2-propanone, N,N-dimethylformamide, N,N-dimethylacetamide, dimethyl sulfoxide and the like, or mixtures thereof. Such solvents may also be used in admixture with other reaction-inert solvents such as, for example, aliphatic-, alicyclic- and aromatic hydrocarbon, e.g., hexane, cyclohexane, benzene, petroleumether and the like. Appropriate bases which may advantageously be used include alkali and earth alkaline metal carbonates, hydrogen carbonates, hydrides and the like, e.g., sodium carbonate, sodium hydrogen carbonate, potassium carbonate, sodium hydride and the like.

The compounds of formula (I) can even so be prepared by reacting an appropriately substituted benzenamine of formula (VI) with a reagent of formula (VII).

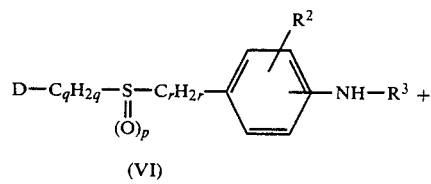

(VI)

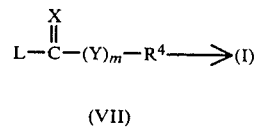

(VII)

In the formulae (VI) and (VII) D, q, p, r, $R^2$, $R^3$, X, Y, m and $R^4$ are as previously described and L is chloro, bromo, iodo, lower alkyloxy, aryloxy, aryllower alkyloxy or a radical of formula

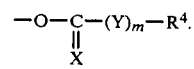

The reaction of (VI) and (VII) can be carried out following art-known procedures of converting carboxylic acids, esters, acyl halides or acid anhydrides into amides, e.g., by stirring the reactants together, if desired, in a suitable solvent such as, for example, benzene, dichloromethane, trichloromethane, pyridine and the like, or a mixture of these solvents. Preferably, the reaction is carried out in the presence of an appropriate base such as, for example, an alkali or earth alkaline metal carbonate, hydrogen carbonate or hydroxide, e.g., potassium carbonate, sodium hydrogen carbonate, potassium hydroxide and the like. In some cases it may be advantageous to carry out the reaction in a two-phase system, formed by water and a water-immiscible inert organic solvent.

The compounds of formula (I) wherein m is 0, said compounds being represented by the formula (I-b), can additionally be prepared by reacting a benzenamine of formula (VI) with a carboxylic acid of formula (VII) following art-known procedures of converting an amine into an amide.

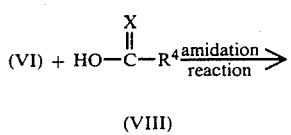

(VIII)

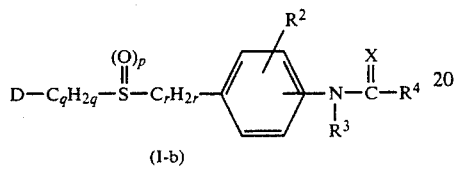

(I-b)

The reaction of (VI) with (VIII) can generally be carried out by stirring and heating the reactants together, if desired, in the presence of a suitable solvent. Preferred reaction temperatures are comprised between 170° C. and 270° C. Suitable solvents are, for example, hydrocarbon mixtures having a boiling range higher than 170° C., dimethyl sulfoxide, 1,2-diethoxyethane and the like.

The compounds of formula (I) wherein m is 1 and Y represents a —NH-radical, said compounds being represented by the formula (I-c), can be prepared by reacting a benzenamine of formula (VI) with a reagent of formula (IX).

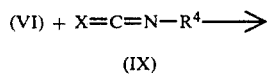

(IX)

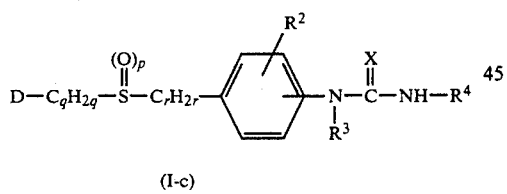

(I-c)

In the above reaction-scheme $R^4$, X, D, q, p, r, $R^2$ and $R^3$ are as previously described. Depending upon the nature of $R^4$ and X the reagent of formula (IX) may also be present in its isomeric form: $R^4$—X—C≡N.

The reaction of (VI) with (IX) can generally be carried out by stirring and, if desired, heating the reactants together in a suitable reaction-inert solvent such as, for example, dichloromethane, 1,4-dioxane and the like. Preferably, the reaction is carried out in the presence of an appropriate base, e.g., N,N-diethylethanamine and the like. The reagent of formula (IX) wherein $R^4$ is hydrogen, may be generated in situ from a corresponding alkali metal cyanate or thiocyanate, e.g., potassium cyanate, sodium thiocyanate and the like.

The compounds of formula (I) wherein $R^3$ is hydrogen and m is 1, said compounds being represented by the formula (I-d), can also be prepared by the addition-reaction of an appropriately substituted isocyanato- or isothiocyanatobenzene of formula (X) with a reagent of formula (XI).

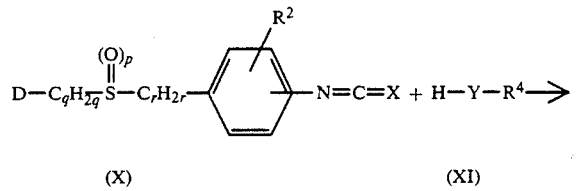

(X)    (XI)

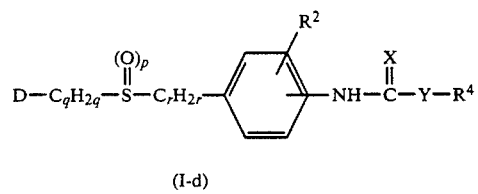

(I-d)

The addition reaction of (X) with (XI) can generally be carried out by stirring and, if desired, heating the reactants together in a suitable solvent such as, for example, water, acetic acid, a halogenated hydrocarbon, e.g., dichloromethane and the like, a cyclic ether, e.g., 1,4-dioxane and the like. In some cases it may be advantageous to convert previously the reagent (XI) into its anion form $\ominus YR^4$.

The compounds of formula (I) wherein $R^3$ is hydrogen, said compounds being represented by the formula (I-e), can be converted into a compound of formula (I) wherein $R^3$ is other than hydrogen, said $R^3$ being represented by $R^{3-a}$ and said compound by the formula (I-f), by reacting (I-e) with a reagent of formula (XII).

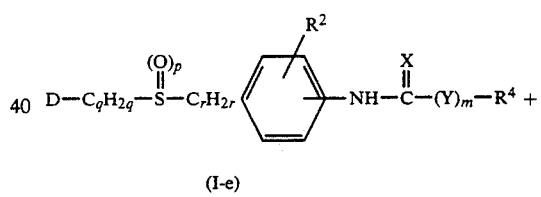

(I-e)

$R^{3-a}W \longrightarrow$

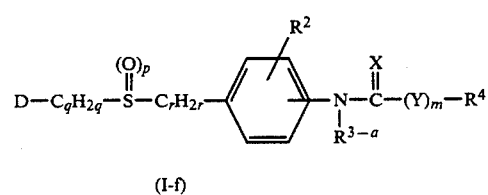

(I-f)

The reaction of (I-e) and (XII) can generally be carried out following art-known N-alkylating procedures as previously described for the preparation of (I) starting from (II) and (III).

The compounds of formula (I) wherein m is 1 may be converted into other compounds of formula (I) by stirring the former with an excess of an appropriate thiol, alcohol or amine, if desired, in a suitable reaction-inert solvent. Some elevated temperatures may enhance the rate of the reaction.

The compounds of formula (I) wherein p is 1 or 2, said compounds being represented by the formula (I-g-1), respectively (I-g-2), can be prepared by oxidizing a compound of formula (I-a) with an appropriate oxidizing agent.

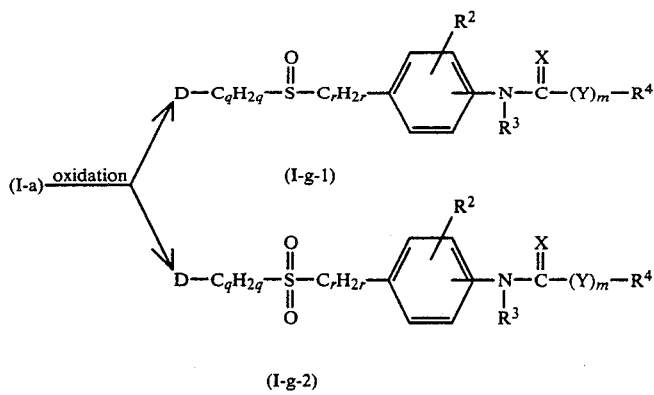

The compounds of formula (I-a) can be oxidized to obtain either a compound of formula (I-g-1) or (I-g-2) depending upon the nature of the oxidizing agent and depending upon the reaction circumstances. Appropriate oxidizing agents are, for example, alkali metal periodates, e.g., sodium periodate, potassium periodate and the like, and peroxides, e.g., hydrogen peroxide and the like.

From formula (I) it is evident that the compounds of this invention have at least two asymmetric carbon atoms in their structure, namely those located in the 2- and 4-positions of the dioxolane nucleus, and consequently they can exist under different stereochemically isomeric forms. The stereochemically isomeric forms of (I) and the pharmaceutically acceptable acid addition salts thereof are intended to be embraced within the scope of this invention.

The diastereomeric racemates of (I), denoted as cis and trans forms respectively, according to the rules described in C.A., 76, Index Guide, Section IV, p. 85 (1972), may be obtained separately by conventional methods. Appropriate methods which may advantageously be employed therefore include, for example, selective crystallization and chromatography separation, e.g., column-chromatography.

Since the stereochemical configuration is already fixed in the intermediates (II), (IV), (VI) and (X) it is also possible to separate cis and trans forms at this or even an earlier stage, whereupon the corresponding forms of (I) may be derived therefrom in the previously indicated manner.

The separation of cis and trans forms of such intermediates may be performed by conventional methods as described hereabove for the separation of cis and trans forms of the compounds (I).

It is evident that the cis and trans diastereomeric racemates may be further resolved into their optical isomers, cis (+), cis (−), trans (+) and trans (−) by the application of methodologies known to those skilled in the art.

The compounds of formula (I) have basic properties and thus may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; and organic acid such as acetic, propanoic, hydroxyacetic, 2-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenyl-2-propenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

A number of the intermediates and starting materials used in the foregoing preparations are known compounds, others may be prepared according to art-known methodologies of preparing similar compounds and some of them are novel and consequently their preparations will be described hereafter.

The intermediates of formula (II) wherein p is 0, (II-a), can be prepared by reacting an appropriately substituted reactive ester of formula (XIII) with an appropriately substituted benzenethiol of formula (XIV), following the same procedure as previously described for the preparation of (I) starting from (IV) and (V).

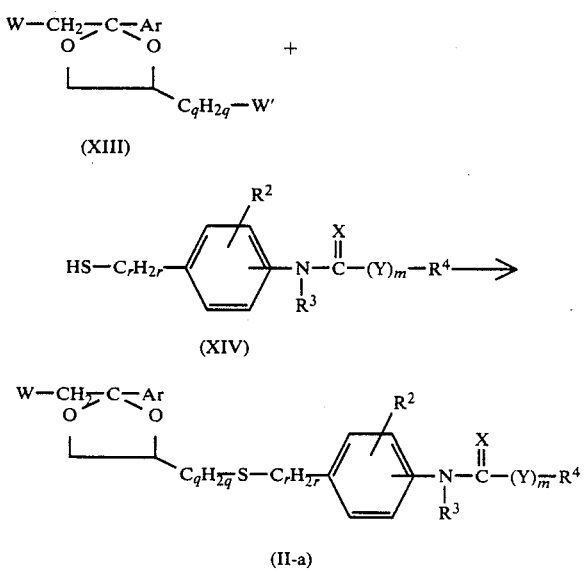

In the formula (XIII) W and W' represent each a reactive leaving group as previously described for W, provided that W' has a higher leaving capacity than W.

The reactive ester (XIII), used as starting material herein, can be derived from the corresponding alcohol (XV) following art-known procedures for converting hydroxyl groups into reactive leaving groups.

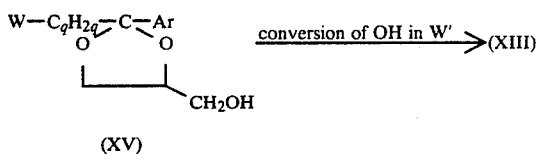

The alcohols (XV), used as starting materials herein, as well as the intermediates of formula (IV), can be prepared following the same procedure as described, for example, in U.S. Pat. No. 4,144,346.

The intermediates of formula (V) can be derived from an appropriately substituted aniline (XVI) as illustrated in the following reaction scheme.

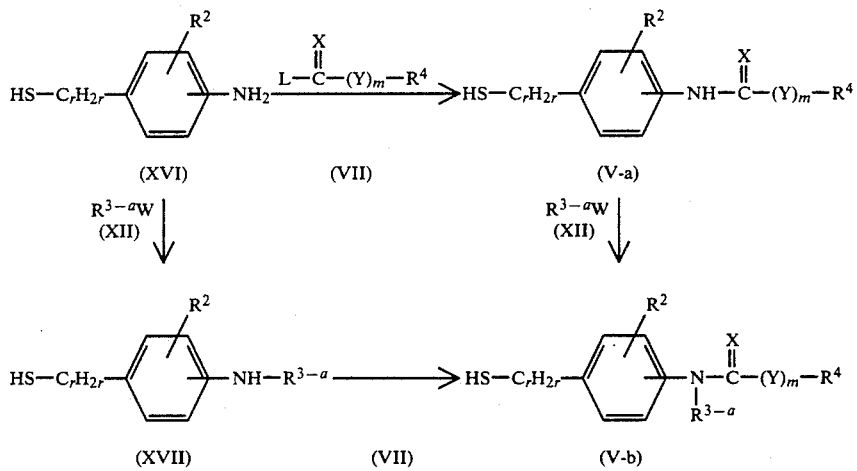

The intermediates of formula (V) wherein $R^3$ is hydrogen, (V-a), can be prepared by reacting (XVI) with (VII) following art-known N-acylating procedures. Said (V-a) may be converted into an intermediate of formula (V) wherein $R^3$ is other than hydrogen, said $R^3$ being represented by $R^{3-a}$ and said intermediates by the formula (V-b), by N-alkylating (V-a) with (XII). Alternatively (V-b) may be derived from (XVI) by previously N-alkylating (XVI) with (XII) and subsequently reacting the thus obtained (XVII) with (VII) following art-known N-acylating procedures.

The intermediates of formula (VI) wherein p is 0, (VI-a), can be prepared by S-alkylating an appropriately substituted benzenethiol (XVII) or (XVI) with a reagent of formula (IV) following the same procedure as as previously described for the preparation of (I-a) starting from (IV) and (V).

The intermediates of formula (VI) wherein p is 1 or 2, (VI-b), can be derived from (VI-a) by oxidizing the latter following art-known procedures as described hereinabove for the preparation of (I-g-1) and (I-g-2) starting from (I-a).

The intermediates of formula (X) can be prepared by reacting an appropriately substituted intermediate (VI) with carbonic dichloride or carbonothioic dichloride following art-known procedures of converting amines into isocyanates or isothiocyanates.

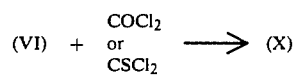

The benzenethiols (V), (XIV), (XVI) and (XVII) used as starting materials in the foregoing reactions or used as intermediates can also be derived from the corresponding phenols following art-known procedures as described, for example, in J. Org. Chem., 31, 3980–3984 (1966).

The compounds of formula (I) and the pharmaceutically acceptable acid addition salts thereof are useful agents in combating fungi and bacteria. For example, said compounds and acid addition salts thereof are found to be highly active against a wide variety of fungi such as, for example, *Microsporum canis, Ctenomyces mentagrophytes, Trichophyton rubrum, Phialophora verrucosa, Cryptococcus neoformans, Candida tropicalis, Candida albicans,* Mucor species, *Aspergillus fumigatus, Sporotrichum schenckii* and Saprolegnia species, and against bacteria such as, for example, *Erysipelotrix insidiosa,* Staphylococci such as *Staphylococcus hemolyticus* and Streptococci such as *Streptococcus pyogenes.* In view of their potent, local as well as systemic, anitmicrobial activity the compounds of this invention constitute useful tools for the destruction and/or the prevention of the growth of fungi and bacteria and more particularly they can effectively be used in the treatment of subjects suffering from such microorganism.

The strong antimicrobial activity of the compounds (I) is clearly evidenced by the data obtained in the following experiments, which data is only given to illustrate the useful antimicrobial properties of all the compounds (I) and not to limit the invention either with respect to the scope of susceptible microorganisms nor with respect to the scope of formula (I).

Tests for the control of fungal organisms are performed using Sabouraud's liquid medium (1 g. of neopeptone Difco and 2 g. of glucose Difco per 100 ml. distilled water) in test tubes, each containing 4.5 ml. of liquid medium, autoclaved at 120° C. for 15 minutes. The azoles are prepared for testing by dissolving in 50% ethanol to a concentration of 20 mg/ml. and thereafter diluting with sterile distilled water to obtain a concentration of 10 mg/ml. Successive decimal dilutions are then made with sterile distilled water to prepare a series of test solutions. In carrying out the test, 0.5 ml. of one of the test solutions is added to 4.5 ml. of Sabouraud's liquid medium to obtain a test medium. In this manner, from appropriate test solutions test media containing 100 μg, 10 μg and 1 μg of azole per milliliter of medium are obtained. Control tubes are prepared by adding 0.5 ml. of sterile distilled water to 4.5 ml. of medium. Ethanol is also added to simulate the amount which would be present in the test media, Filamentous fungi are incubated at 25° C. for two to three weeks. A square block of side 2 mm. is excised and inoculated into the liquid medium. A 3-day old culture on Sabouraud's liquid medium is used for yeasts. The inoculum is 0.05 ml. per tube. All cultures are incubated at 25° C. for 14 days.

Table I illustrates the high effectiveness of a number of compounds of formula (I), their acid addition salts and their stereochemically isomeric forms against a number of species of fungi. The columns 1, 2, 3 and 4 show the minimal doses (in μg/ml) which are effective in inhibiting the growth of *Microsporum canis,* respectively, *Ctenomyces mentagrophytes, Cryptococcus neoformans* and *Candida albicans.*

The data in table I are intended to illustrate but not to limit the scope of the present invention.

TABLE I

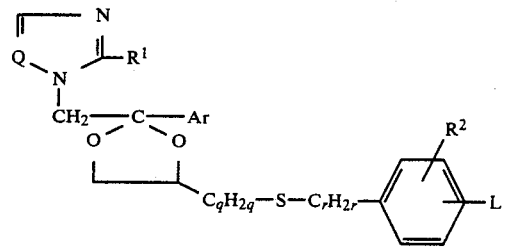

| Q | L | Ar | $R^1$ | $R^2$ | q | r | base/salt form | isomeric form | antifungal activity expressed in μg/ml. | | | |
|---|---|---|---|---|---|---|---|---|---|---|---|---|
| | | | | | | | | | M.c. | C.m. | C.n. | C.a. |
| CH | 4-NH—COCH$_3$ | 2,4-Cl$_2$—C$_6$H$_3$ | H | H | 1 | 0 | HCl | cis | 10 | <1 | 1 | <1 |
| CH | 4-NH—CHO | 2,4-Cl$_2$—C$_6$H$_3$ | H | H | 1 | 0 | base | cis | 100 | <1 | 1 | <1 |
| CH | 4-NH—COOCH$_3$ | 2,4-Cl$_2$—C$_6$H$_3$ | H | H | 1 | 0 | base | cis | — | <1 | 10 | 100 |
| CH | 4-NH—COOC$_2$H$_5$ | 2,4-Cl$_2$—C$_6$H$_3$ | H | H | 1 | 0 | base | cis | 100 | <1 | 10 | 100 |
| CH | 4-NH—CS—NH—NH$_2$ | 2,4-Cl$_2$—C$_6$H$_3$ | H | H | 1 | 0 | base | cis | 100 | <1 | 10 | <1 |
| CH | 4-NH—CO—C$_2$H$_5$ | 2,4-Cl$_2$—C$_6$H$_3$ | H | H | 1 | 0 | (COOH)$_2$ | cis | 100 | <1 | 1 | <1 |
| CH | 4-NH—CONH$_2$ | 2,4-Cl$_2$—C$_6$H$_3$ | H | H | 1 | 0 | base ½ H$_2$O | cis | — | 10 | — | 10 |
| CH | 4-NH—CS—NHCH$_3$ | 2,4-Cl$_2$—C$_6$H$_3$ | H | H | 1 | 0 | base | cis | — | 1 | 10 | <1 |
| CH | 4-NH—CS—NH$_2$ | 2,4-Cl$_2$—C$_6$H$_3$ | H | H | 1 | 0 | base | cis | — | 100 | — | 10 |
| N | 4-NH—CO—C$_2$H$_5$ | 2,4-Cl$_2$—C$_6$H$_3$ | H | H | 1 | 0 | base | cis | — | 10 | — | <1 |
| N | 4-NH—CHO | 2,4-Cl$_2$—C$_6$H$_3$ | H | H | 1 | 0 | base | cis | — | <1 | 100 | <1 |
| N | 4-NH—COCH$_3$ | 2,4-Cl$_2$—C$_6$H$_3$ | H | H | 1 | 0 | base | cis | — | 10 | — | 1 |
| N | 4-NH—COOC$_2$H$_5$ | 2,4-Cl$_2$—C$_6$H$_3$ | H | H | 1 | 0 | base | cis | — | 1 | 10 | 10 |
| CH | 4-NHCOOC$_2$H$_5$ | 2,4-Cl$_2$—C$_6$H$_3$ | H | H | 1 | 0 | HCl.H$_2$O | cis | — | 100 | 10 | <1 |
| CH | 4-NH—CONHCH$_3$ | 2,4-Cl$_2$—C$_6$H$_3$ | H | H | 1 | 0 | HCl | cis | 100 | 1 | 10 | 100 |
| CH | 4-NH—COOCH$_2$CH$_2$—O—CH(CH$_3$)$_2$ | 2,4-Cl$_2$—C$_6$H$_3$ | H | H | 1 | 0 | base/ 2H$_2$O | cis | — | 100 | 100 | 1 |
| CH | 4-NHCOOCH(CH$_3$)C$_2$H$_5$ | 2,4-Cl$_2$—C$_6$H$_3$ | H | H | 1 | 0 | base | cis | — | 10 | 1 | 100 |
| CH | 4-NH—CS—N(C$_2$H$_5$)$_2$ | 2,4-Cl$_2$—C$_6$H$_3$ | H | H | 1 | 0 | base | cis | 100 | 10 | 1 | 10 |
| CH | 2-NH—COOCH$_3$ | 2,4-Cl$_2$—C$_6$H$_3$ | H | H | 1 | 0 | base | cis | 10 | <1 | 10 | 100 |
| CH | 4-NH—CO—CH$_3$ | 2,4-Cl$_2$—C$_6$H$_3$ | H | H | 1 | 0 | base | trans | — | <1 | 100 | 100 |
| CH | 4-NH—CS—OCH$_3$ | 2,4-Cl$_2$—C$_6$H$_3$ | H | H | 1 | 0 | base | cis | — | 100 | 10 | 10 |
| CH | 4-NHCOOCH$_2$CH=CH$_2$ | 2,4-Cl$_2$—C$_6$H$_3$ | H | H | 1 | 0 | base | cis | — | 10 | 10 | <1 |
| CH | 4-NH—COOCH$_2$CH$_2$—COOC$_2$H$_5$ | 2,4-Cl$_2$—C$_6$H$_3$ | H | H | 1 | 0 | base | cis | 100 | 1 | 1 | <1 |
| CH | 4-NH—COOC$_2$H$_5$ | 2,4-Cl$_2$—C$_6$H$_3$ | H | H | 1 | 0 | base | trans | — | 10 | 10 | 100 |
| CH | 4-NHCOOCH$_3$ | 2,4-Cl$_2$—C$_6$H$_3$ | H | H | 1 | 0 | base | trans | 100 | <1 | <1 | — |
| CH | 4-NHCOOCH$_2$CH$_2$—OCH$_3$ | 2,4-Cl$_2$—C$_6$H$_3$ | H | H | 1 | 0 | base | cis | — | <1 | <1 | <1 |
| CH | 4-NHCOOCH$_2$CH$_2$—OC$_2$H$_5$ | 2,4-Cl$_2$—C$_6$H$_3$ | H | H | 1 | 0 | base | cis | — | 10 | 10 | <1 |
| CH | 4-N(CH$_3$)—COOC$_2$H$_5$ | 2,4-Cl$_2$—C$_6$H$_3$ | H | H | 1 | 0 | 2(COOH)$_2$ | cis | 10 | <1 | <1 | <1 |
| CH | 4-NH—COOCH$_2$CH$_2$—COOCH$_3$ | 2,4-Cl$_2$—C$_6$H$_3$ | H | H | 1 | 0 | base | cis | 100 | <1 | 1 | <1 |
| CH | 4-NH—COOCH$_2$—COOC$_2$H$_5$ | 2,4-Cl$_2$—C$_6$H$_3$ | H | H | 1 | 0 | base | cis | 100 | 10 | 100 | 1 |
| CH | 4-N(C$_2$H$_5$)COOC$_2$H$_5$ | 2,4-Cl$_2$—C$_6$H$_3$ | H | H | 1 | 0 | 3½(COOH)$_2$ | cis | 100 | <1 | 1 | <1 |
| CH | 4-NHCOOCH$_2$CH$_2$S—CH$_3$ | 2,4-Cl$_2$—C$_6$H$_3$ | H | H | 1 | 0 | base | cis | — | 10 | 10 | 100 |
| CH | 4-N(CH$_3$)COOCH$_3$ | 2,4-Cl$_2$—C$_6$H$_3$ | H | H | 1 | 0 | 2(COOH)$_2$ | cis | 10 | <1 | 10 | <1 |
| CH | 4-N(C$_2$H$_5$)COOC$_2$H$_5$ | 2,4-Cl$_2$—C$_6$H$_3$ | H | H | 1 | 0 | 1½(COOH)$_2$ | cis | 10 | <1 | <1 | <1 |
| CH | 4-NH—COOCH$_3$ | 2,4-Cl$_2$—C$_6$H$_3$ | H | 3-CH$_3$ | 1 | 0 | base | cis | 100 | <1 | 10 | 100 |
| CH | 4-NH—COOCH$_3$ | 2,4-Cl$_2$—C$_6$H$_3$ | H | 3-Cl | 1 | 0 | base | cis | 100 | <1 | 10 | 100 |
| CH | 4-NH—COOC$_2$H$_5$ | 2,4-Cl$_2$—C$_6$H$_3$ | H | 3-Cl | 1 | 0 | base | cis | — | <1 | 1 | <1 |
| CH | 4-NH—COOCH$_3$ | 2,4-Cl$_2$—C$_6$H$_3$ | H | H | 1 | 1 | 3(COOH)$_2$ 3H$_2$O | cis | 100 | <1 | <1 | 100 |
| CH | 4-NH—COOC$_2$H$_5$ | 2,4-Cl$_2$—C$_6$H$_3$ | H | H | 1 | 1 | 4(COOH)$_2$ 4H$_2$O | cis | 100 | <1 | <1 | 10 |
| CH | 4-NH—COOC$_2$H$_5$ | 2,4-Cl$_2$—C$_6$H$_3$ | C$_2$H$_5$ | H | 1 | 0 | base | cis | — | 10 | — | 100 |
| CH | 4-NH—COOC$_2$H$_5$ | 2-Cl,4-Br—C$_6$H$_3$ | H | H | 1 | 0 | base | cis | — | 100 | 10 | — |
| CH | 4-NH—COOC$_2$H$_5$ | 2-Cl,4-CH$_3$O—C$_6$H$_3$ | H | H | 1 | 0 | base | cis | — | 100 | 10 | — |
| CH | 4-NH—COOC$_2$H$_5$ | 2,4-Cl$_2$—C$_6$H$_3$ | H | H | 2 | 0 | 1½(COOH)$_2$ | cis | — | 10 | <1 | — |

TABLE I-continued

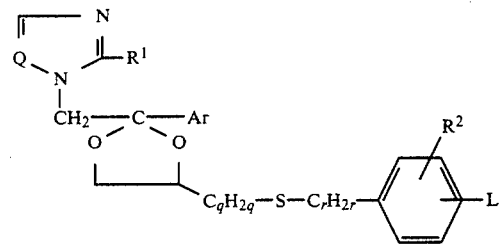

| Q | L | Ar | R¹ | R² | q | r | base/salt form | isomeric form | M.c. | C.m. | C.n. | C.a. |
|---|---|---|---|---|---|---|---|---|---|---|---|---|
| CH | 4-NH—COOC$_2$H$_5$ | 2-Cl,4-F—C$_6$H$_3$ | H | H | 1 | 0 | base | cis | — | 10 | — | 100 |
| N | 4-NH—COOC$_2$H$_5$ | 2,4-Cl$_2$—C$_6$H$_3$ | H | H | 2 | 0 | (COOH)$_2$ | cis | — | 10 | <1 | — |

In view of their antifungal and antibacterial properties this invention provides valuable compositions comprising the subject compounds of formula (I) or acid addition salts thereof as the active ingredient in a solvent or a solid, semi-solid or liquid diluent or carrier, and, in addition, it provides an effective method of combating fungal or bacterial growth by use of an effective antifungal or antibacterial amount of such compounds (I) or salts thereof. Antifungal and antibacterial compositions comprising an effective amount of an active compound (I), either alone or in combination with other active therapeutic ingredients, in admixture with suitable carriers may be readily prepared according to conventional pharmaceutical techniques for the usual routes of administration. Preferred compositions are in dosage unit form, comprising per dosage unit an effective quantity of the active ingredient in admixture with suitable carriers. Although the amount of the active ingredient per unit dosage may vary within rather wide limits, dosage units comprising from about 50 to about 500 mg and more particularly from about 100 to about 250 mg of the active ingredient are preferred.

The compounds of formula (I), the acid addition salts and stereochemically isomeric forms thereof are also useful agents for aiding regression and palliation of neoplastic diseases in animal and human hosts.

Neoplastic disease, as used herein, is meant to include all types of cancerous growths or oncogenic processes, metastatic tissues or malignantly transformed cells, tissues or organs, irrespective of histopathologic type or stage of invasiveness. For example, the subject compounds may be used in accordance with this invention against such neoplastic disorders as "Lewis Lung 3 LL" tumor and pulmonary metastases, methylcholanthrene induced sarcoma, Moloney leukemia, sarcoma 180, leukemia L 1210 and the like in laboratory animals.

A particularly useful test is against lymphoid L 1210 in mice, which has been shown to have the highest predictability value of animal tumor screens for clinical activity against myclocytic leukemia, lymphoma, multiple myeloma, carcinoma of the ovary, colon or breast, Wilm's tumor, neuroblastoma and choriocarcinoma (see, for example, Cancer Chemotherapy Reports, Vol. 50, 173–218 (1966).

Another useful test is against fibronarcioma MO-4 in mice, which has been shown to be predictive for antineoplastic chemotherapeuthic agents like cyclophosphamide (see Merck Index, 7th volume, page 313), which is an alkylating antineoplastic agent in lymphomas and certain leukemias.

EXPERIMENT 1

MO$_4$-in vivo-screening

MO$_4$ cells are C$_3$H mouse embryonal cells that have been transformed by the Kirsten strain of murine sarcoma virus. They are routinely subcultered in Eagle's minimal essential medium supplemented with 10% fetal bovine serum. For inocculation in inbred C$_3$H mice the cells are trypsinized and suspended in complete medium. They are spun down (800 rpm), washed once in Eagle's minimal essential medium without serum and diluted in the same medium at a concentration of 5.10$^6$ cells per ml. C$_3$H mice are inoculated with 0.2 ml of the cell suspension (1.10$^6$ cells/mouse) by intraperitoneal injection. With this cell inoculum the control mice die after 16–20 days with many tumour nodules on the serous membranes all through the peritoneal cavity and with accumulation of ascitic fluid. The test compounds are administered by intraperitoneal injection (40 mg/kg). Survival time is recorded and the results are expressed as T/c ratios of the medium survival time (T=treated; c=control). The T/c ratios of a number of compounds are illustrated in column 1 of table II.

EXPERIMENT 2

L 1210-in vivo-screening

L 1210 mouse leukemia cells are transplanted intraperitoneally in DBA$_2$/C$_3$H mice and collected once a week by rincing the peritoneum with sterile saline. The cells are centrifuged, resuspended in Eagle's minimal essential medium (without serum) and diluted to a concentration of 5×10$^6$ cells/ml. Each mouse (DBA$_2$/C$_3$HF$_1$ hybrid) receives 0.2 ml cell suspension intraperitoneally or intravenously. The test compounds are administered by intraperitoneal injection (40 mg/kg). Survival time is recorded and the results are expressed as T/c ratios of the medium survival time (T=treated, c=control). The T/c ratios of a number of compounds are illustrated in column 2 of table II.

The data in table II are intended to illustrate but not to limit the scope of the present invention.

TABLE II

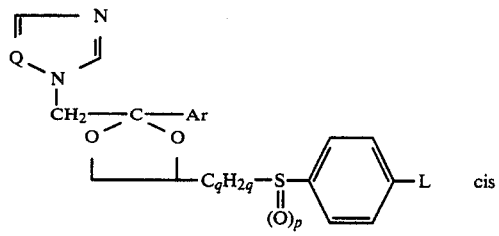

| Q | L | q | p | base/salt form | Ar | T/c MO4 | T/c L 1210 |
|---|---|---|---|---|---|---|---|
| CH | NH—COOCH$_3$ | 1 | 0 | base | 2,4-Cl$_2$—C$_6$H$_3$ | 1.38 | 1.50 |
| CH | NH—COOC$_2$H$_5$ | 1 | 0 | base | 2,4-Cl$_2$—C$_6$H$_3$ | 1.86 | 1.88 |
| CH | NH—COOC$_6$H$_5$ | 1 | 0 | base | 2,4-Cl$_2$—C$_6$H$_3$ | 1.64 | — |
| CH | NH—COOC$_2$H$_5$ | 1 | 0 | HCl.H$_2$O | 2,4-Cl$_2$—C$_6$H$_3$ | 1.93 | 2.33 |
| CH | NH—COOCH$_2$CH(CH$_3$)$_2$ | 1 | 0 | base | 2,4-Cl$_2$—C$_6$H$_3$ | 1.83 | 1.67 |
| CH | NH—COOn.C$_5$H$_{11}$ | 1 | 0 | base | 2,4-Cl$_2$—C$_6$H$_3$ | 1.33 | — |
| CH | NH—COOn.C$_3$H$_7$ | 1 | 0 | base | 2,4-Cl$_2$—C$_6$H$_3$ | 1.75 | 2.17 |
| CH | NH—COOi.C$_3$H$_7$ | 1 | 0 | base | 2,4-Cl$_2$—C$_6$H$_3$ | 1.50 | 1.83 |
| CH | NH—COOn.C$_4$H$_9$ | 1 | 0 | base | 2,4-Cl$_2$—C$_6$H$_3$ | 2.17 | 1.75 |
| CH | NH—COOc.C$_5$H$_9$ | 1 | 0 | base | 2,4-Cl$_2$—C$_6$H$_3$ | 1.79 | 1.44 |
| CH | NH—COOCH$_2$CH$_2$Cl | 1 | 0 | base | 2,4-Cl$_2$—C$_6$H$_3$ | 1.69 | 1.81 |
| CH | NH—COO(CH$_2$)$_3$CH$_2$Cl | 1 | 0 | base | 2,4-Cl$_2$—C$_6$H$_3$ | 1.27 | — |
| CH | NH—COOCH$_2$CH=CH$_2$ | 1 | 0 | base | 2,4-Cl$_2$—C$_6$H$_3$ | 1.25 | — |
| CH | NH—COOCH$_2$CH$_2$SCH$_2$CH$_3$ | 1 | 0 | base | 2,4-Cl$_2$—C$_6$H$_3$ | 1.67 | — |
| CH | NH—COOCH$_2$CH$_2$SCH$_3$ | 1 | 0 | base | 2,4-Cl$_2$—C$_6$H$_3$ | 1.36 | — |
| CH | NH—COOC$_2$H$_5$ | 1 | 2 | base | 2,4-Cl$_2$—C$_6$H$_3$ | 1.36 | — |
| CH | NH—COOC$_2$H$_5$ | 2 | 0 | base | 2-Cl,4-F—C$_6$H$_3$ | 1.25 | 1.14 |
| CH | NH—COOC$_2$H$_5$ | 1 | 0 | base | 2-Cl,4-Br—C$_6$H$_3$ | 1.19 | — |

In tests based on the structure or the function of microtubules, as described in Journal of the National Cancer Institute, 56, (2), 357–363 (1976) and 61, (3), 787–792 (1978), the subject compounds display an important inhibiting affect on the formation of microtubules and, subsequently, the subject compounds have useful properties as inhibitors of the formation of metastatic tissues and they dramatically interfere with the cell-splitting process so that said compounds can be used to inhibit the growth of tumors.

The process of this invention comprises systemically administering to subjects hosting neoplastic disease an effective ameliorating amount of a compound of formula (I), preferably admixed with a pharmaceutically acceptable carrier. Such carrier may take a wide variety of forms depending on the form of preparation desired for administration, i.e., oral or parenteral. In preparing the compositions in oral dosage form, any of the usual pharmaceutical media may be employed, such as, for example, water, glycols, oils, alcohols, and the like in the case of oral liquid preparations such as suspensions, elixirs and solutions; or solid carriers such as starches, sugars, kaolin, lubricants, binders, disintegrating agents and the like in the case of powders, capsules and tablets. Because of their ease in administration, tablets and capsules represent the most advantageous oral dosage form, in which case solid pharmaceutical carriers are obviously employed. For parenteral injection, the carrier will usually comprise sterile water, at least in large part, though other ingredients, for example, to aid solubility may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

It is especially advantageous to formulate the aforementioned pharmaceutical compositions in dosage unit form for ease of administration and uniformity of dosage. Dosage unit form, as used herein, refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder, packets, wafers, teaspoonfuls, tablespoonfuls and the like, and segregated multiples thereof. The amount of active ingredient per dosage unit may range from about 5 mg to about 500 mg, and, preferably, from about 10 mg to about 250 mg.

The total dosage of the active ingredient for the treatment of the particular neoplastic disease may depend on the species and size of the subject being treated; the particular condition and its severity; the particular solubility of the active ingredient and the route of administration. In any case the dose to be used is one non-toxic to the recipient.

As a dosage regimen, the amount of principal active ingredient systemically administered is an effective amount sufficient to aid regression and palliation of the neoplastic disease in the absence of excessive deleterious side effects of a cyctotoxic nature to the host harboring the disease.

The examples are intended to illustrate but not to limit the scope of the present invention.

A. PREPARATION OF INTERMEDIATES

EXAMPLE I

139 Parts of phosgene are introduced through 150 parts of 2-phenoxyethanol at room temperature (exothermic reaction: cooling on a water-bath is necessary). The reaction mixture is poured onto ice-water. The organic phase is separated, dried, filtered and evaporated. The residue is distilled, yielding 106 parts of 2-phenoxyethyl chloroformate; bp. 135°–140° C. (water-jet).

EXAMPLE II

To a stirred mixture of 15 parts of 4-aminobenzenethiol, 10.9 parts of sodium hydrogen carbonate and 260 parts of dichloromethane are added dropwise 14 parts of ethyl carbonochloridate. Upon completion, stirring is continued overnight at room temperature. The reaction mixture is poured onto water and the whole is neutralized with sodium hydrogen carbonate. The organic phase is separated, dried, filtered and evaporated. The residue is triturated in petroleumether. The product is filtered off and stirred in 2,2′-oxybispropane. The mixture is filtered and the filtrate is evaporated. The residue is crystallized from petroleumether, yielding 20.8 parts of ethyl (4-mercaptophenyl)carbamate.

EXAMPLE III

A mixture of 10 parts of 1,2,3-propanetriol, 27 parts of 2-bromo-1-(2,4-dichlorophenyl)ethanone, 2 parts of 4-methylbenzenesulfonic acid, 40 parts of 1-butanol and 225 parts of methylbenzene is stirred and refluxed overnight with water-separator. The reaction mixture is cooled, washed with a potassium carbonate solution, dried, filtered and evaporated. The residue is distilled, yielding 21.5 parts (69%) of (A+B)-2-(bromomethyl)-2-(2,4-dichlorophenyl)-1,3-dioxolane-4-methanol; bp. 145°–150° C. at 0.05 mm pressure.

EXAMPLE IV

A mixture of 32 parts of 1,2,3-propanetriol, 5 parts of 4-methylbenzenesulfonic acid and 450 parts of benzene is distilled azeotropically to dry for 2 hours. After cooling, 19.9 parts of (2-chloro-4-nitrophenyl)ethanone are added and stirring is continued overnight at reflux temperature. The mixture is cooled and there are added dropwise 15.9 parts of bromine. Upon completion, stirring is continued for 2 hours at reflux temperature. The reaction mixture is cooled, poured onto water and 30 parts of a sodium hydroxide solution 5% are added. The product is extracted twice with dichloromethane. The combined extracts are washed with water, dried, filtered and evaporated. The residue is purified by column-chromatography over silica gel using a mixture of trichloromethane and methanol (99.5:0.5 by volume) as eluent. The pure fractions are collected and the eluent is evaporated, yielding 13.2 parts of (cis+trans)-2-(bromomethyl)-2-(2-chloro-4-nitrophenyl)-1,3-dioxolane-4-methanol as an oily residue.

EXAMPLE V

To a stirred mixture of 21.5 parts of (A+B)-2-(bromomethyl)-2-(2,4-dichlorophenyl)-1,3-dioxolane-4-methanol and 50 parts of pyridine are added dropwise 11.5 parts of benzoyl chloride. Upon completion, stirring is continued for 1 hour at room temperature. The reaction mixture is poured onto water and the product is extracted twice with 1,1′-oxybisethane. The combined extracts are washed twice with a diluted hydrochloric acid solution and once with water, dried, filtered and evaporated. The residue is triturated in methanol. The product is filtered off and crystallized from methanol, yielding 12 parts (39%) of cis-2-(bromomethyl)-2-(2,4-dichlorophenyl)-1,3-dioxolan-4-ylmethyl benzoate; mp. 117.7° C.

In a similar manner there are also prepared:
cis-2-(bromomethyl)-2-(2-chloro-4-nitrophenyl)-1,3-dioxolane-4-methanol benzoate (ester); mp. 140.6° C.; and
cis-2-(4-bromophenyl)-2-(1H-imidazol-1-ylmethyl)-1,3-dioxolane-4-methanol benzoate (ester) as a residue.

EXAMPLE VI

A mixture of 4.5 parts of trans-2-(bromomethyl)-2-(2,4-dichlorophenyl)-1,3-dioxolan-4-ylmethyl benzoate (ester), 3 parts of sodium hydroxide solution 60%, 60 parts of water and 100 parts of 1,4-dioxane is stirred and refluxed for one hour. The reaction mixture is cooled, poured onto water and the product is extracted with trichloromethane. The extract is washed with water, dried, filtered and evaporated, yielding 1.6 parts of trans-2-(bromomethyl)-2-(2,4-dichlorophenyl)-1,3-dioxolane-4-methanol as an oily residue.

In a similar manner there is also prepared:
cis-2-(4-bromophenyl)-2-(1H-imidazol-1-ylmethyl)-1,3-dioxolane-4-methanol as a residue.

EXAMPLE VII

To a stirred mixture of 40 parts of trans-2-(bromomethyl)-2-(2,4-dichlorophenyl)-1,3-dioxolane-4-methanol, 150 parts of pyridine and 195 parts of dichloromethane are added dropwise 20 parts of methanesulfonyl chloride. Upon completion, stirring is continued overnight at room temperature. The reaction mixture is poured onto water and the product is extracted with dichloromethane. The extract is washed with a dilute hydrochloric acid solution and with water, dried, filtered and evaporated, yielding 56 parts of trans-2-(bromomethyl)-2-(2,4-dichlorophenyl)-1,3-dioxolane-4-methanol methanesulfonate (ester) as a residue.

EXAMPLE VIII

A mixture of 2 parts of N-(4-mercaptophenyl)acetamide, 4 parts of trans-2-(bromomethyl)-2-(2,4-dichlorophenyl)-1,3-dioxolane-4-methanol methanesulfonate (ester), 2 parts of potassium carbonate and 80 parts of 2-propanone is stirred and refluxed overnight. The reaction mixture is cooled and filtered. The filtrate is washed with 2-propanone and evaporated. The residue is purified by column-chromatography over silica gel using a mixture of trichloromethane and methanol (98:2 by volume) as eluent. The pure fractions are collected and the eluent is evaporated. The residue is triturated in a mixture of 2,2′-oxybispropane and petroleumether. The product is filtered off and dried in vacuo at room temperature, yielding 2.9 parts of trans-N-[4-[2-(bromomethyl)-2-(2,4-dichlorophenyl)-1,3-dioxolan-4-ylmethylthio]phenyl]acetamide; mp. 91.5° C.

EXAMPLE IX

378 Parts of tetrahydrothiophene 1,1-oxide are distilled azeotropically to dry with 180 parts of benzene. The latter is evaporated and to the residue are added 45 parts of 2-methyl-1H-imidazole and 45 parts of cis-2-(bromomethyl)-2-(2,4-dichlorophenyl)-1,3-dioxolan-4-yl methyl benzoate. The whole is stirred for 2 days at 170° C. under nitrogen atmosphere. After cooling, the reaction mixture is poured onto water and the product is extracted with 2,2′-oxybispropane. The extract is washed with water, dried, filtered and evaporated, yielding 27 parts of cis-2-(2,4-dichlorophenyl)-2-(2-methyl-1H-imidazol-1-ylmethyl)-1,3-dioxolane-4-methanol benzoate (ester) as a residue.

EXAMPLE X

A mixture of 1.6 parts of 1H-1,2,4-triazole, 54 parts of N,N-dimethylformamide and 45 parts of benzene is stirred and refluxed for 2 hours. After cooling, 0.78 parts of sodium hydride dispersion 78% are added and the whole is stirred for 30 minutes at room temperature. Then there are added 8.9 parts of cis-2-(bromomethyl)-2-(2,4-dichlorophenyl)-1,3-dioxolan-4-ylmethyl benzoate and stirring is continued overnight at 150° C. The reaction mixture is cooled and poured onto water. The product is extracted three times with benzene. The combined extracts are washed twice with water, dried, filtered and evaporated, yielding 8.5 parts of cis-2-(2,4-dichlorophenyl)-2-(1H-1,2,4-triazol-1-ylmethyl)-1,3-dioxolane-4-methanol benzoate (ester) as a residue.

EXAMPLE XI

A mixture of 8 parts of 1H-imidazole, 11 parts of cis-2-(bromomethyl)-2-(2,4-dichlorophenyl)-1,3-dioxolan-4-ylmethyl benzoate (ester) and 180 parts of N,N-dimethylacetamide is stirred and refluxed for 4 days. The reaction mixture is cooled and poured onto water. The product is extracted twice with 1,1'-oxybisethane. The combined extracts are washed with water and acidified with a nitric acid solution in 1,1'-oxybisethane. The formed nitrate salt is filtered off and crystallized from a mixture of 2-propanol and 2,2'-oxybispropane, yielding 6.9 parts (56%) of cis-2-(2,4-dichlorophenyl)-2-(1H-imidazol-1-ylmethyl)-1,3-dioxolane-4-methanol benzoate nitrate; mp. 172° C.

In a similar manner there is also prepared:
cis-2-(2,4-dichlorophenyl)-2-(2-ethyl-1H-imidazol-1-ylmethyl)-1,3-dioxolane-4-methanol benzoate (ester) ethanedioate (2:5); mp. 94.4° C.

EXAMPLE XII

A mixture of 22.5 parts of cis-2-(bromomethyl)-2-(2-chloro-4-nitrophenyl)-1,3-dioxolane-4-methanol benzoate (ester), 450 parts of N,N-dimethylacetamide and 90 parts of benzene is distilled azeotropically to dry. Then there are added 17 parts of 1H-imidazole and the whole is stirred and refluxed for 5 days. The reaction mixture is evaporated. The residue is purified by column-chromatography over silica gel using a mixture of trichloromethane and methanol (98:2 by volume) as eluent. The pure fractions are collected and the eluent is evaporated. The residue is crystallized from a mixture of 4-methyl-2-pentanone and 2,2'-oxybispropane. The product is filtered off and dried, yielding 9.7 parts of cis-2-(2-chloro-4-nitrophenyl)-2-(1H-imidazol-1-ylmethyl)-1,3-dioxolane-4-methanol benzoate (ester); mp. 130.6° C.

EXAMPLE XIII

A mixture of 53.5 parts of cis-2-(2,4-dichlorophenyl)-2-(1H-imidazol-1-ylmethyl)-1,3-dioxolane-4-methanol benzoate nitrate, 30 parts of sodium hydroxide solution 50%, 250 parts of 1,4-dioxane and 50 parts of water is stirred and refluxed for 30 minutes. The reaction mixture is cooled to room temperature and poured onto 600 parts of ice-water, while stirring. The precipitated product is filtered off and dissolved in trichloromethane. The solution is dried, filtered and evaporated, yielding 33.5 parts (96%) of cis-2-(2,4-dichlorophenyl)-2-(1H-imidazol-1-ylmethyl)-1,3-dioxolane-4-methanol; mp. 140° C.

Following the same hydrolyzing procedure there are also prepared:
cis-2-(2,4-dichlorophenyl)-2-(1H-1,2,4-triazol-1-ylmethyl)-1,3-dioxolane-4-methanol; mp. 138.2° C.;
cis-2-(2-chloro-4-nitrophenyl)-2-(1H-imidazol-1-ylmethyl)-1,3-dioxolane-4-methanol; mp. 172.1° C.;
cis-2-(2,4-dichlorophenyl)-2-(2-methyl-1H-imidazol-1-ylmethyl)-1,3-dioxolane-4-methanol; mp. 155.9° C.; and
cis-2-(2,4-dichlorophenyl)-2-(2-ethyl-1H-imidazol-1-ylmethyl)-1,3-dioxolane-4-methanol; mp. 142.4° C.

EXAMPLE XIV

A mixture of 4.5 parts of methanesulfonyl chloride, 10 parts of cis-2-(2,4-dichlorophenyl)-2-(1H-imidazol-1-ylmethyl)-1,3-dioxolane-4-methanol and 50 parts of pyridine is allowed to stand for 3 hours at room temperature. The reaction mixture is poured onto water. The precipitated product is filtered off and crystallized from benzene, yielding 10.3 parts (87%) of cis-2-(2,4-dichlorophenyl)-2-(1H-imidazol-1-ylmethyl)-1,3-dioxolane-4-methanol methanesulfonate; mp. 111.7° C.

In a similar manner there are also prepared:
cis-2-(2,4-dichlorophenyl)-2-(1H-1,2,4-triazol-1-ylmethyl)-1,3-dioxolane-4-methanol methanesulfonate (ester); mp. 98° C.;
cis-2-(2-chloro-4-nitrophenyl)-2-(1H-imidazol-1-ylmethyl)-1,3-dioxolane-4-methanol methanesulfonate (ester); mp. 152.4° C.;
cis-2-(2,4-dichlorophenyl)-2-(2-methyl-1H-imidazol-1-ylmethyl)1,3-dioxolane-4-methanol methanesulfonate (ester);
cis-2-(2,4-dichlorophenyl)-2-[(2-ethyl-1H-imidazol-1-yl)methyl]-1,3-dioxolane-4-methanol methanesulfonate (ester);
cis-2-(4-chlorophenyl)-2-(1H-imidazol-1-ylmethyl)-1,3-dioxolane-4-methanol methanesulfonate (ester);
cis-2-(4-bromo-2-chlorophenyl)-2-(1H-imidazol-1-ylmethyl)-1,3-dioxolane-4-methanol methanesulfonate (ester);
cis-2-(bromomethyl)-2-(2-chloro-4-methoxyphenyl)-1,3-dioxolane-4-methanol methanesulfonate (ester);
cis-2-(2-chloro-4-fluorophenyl)-2-(1H-imidazol-1-ylmethyl)-1,3-dioxolane-4-methanol methanesulfonate (ester); and
cis-2-(4-bromophenyl)-2-(1H-imidazol-1-ylmethyl)-1,3-dioxolane-4-methanol methanesulfonate (ester).

EXAMPLE XV

A mixture of 2.5 parts of 3-aminobenzenethiol, 8 parts of cis-[2-(2,4-dichlorophenyl)-2-(1H-imidazol-1-ylmethyl)-1,3-dioxolan-4-ylmethyl]methanesulfonate, 0.8 parts of sodium hydroxide and 80 parts of methanol is stirred and refluxed for 8 hours. The reaction mixture is cooled and poured onto water. The product is extracted with dichloromethane. The extract is washed with a sodium hydroxide solution and with water, dried, filtered and evaporated. The residue is purified by column-chromatography over silica gel using a mixture of trichloromethane and methanol (98:2 by volume) as eluent. The pure fractions are collected and the eluent is evaporated. The residue is triturated in 2-propanol, yielding 4.4 parts of cis-3-[2-(2,4-dichlorophenyl)-2-(1H-imidazol-1-ylmethyl)-1,3-dioxolan-4-ylmethylthio]benzenamine; mp. 131.2° C.

In a similar manner there are also prepared:
cis-2-[2-(2,4-dichlorophenyl)-2-(1H-imidazol-1-ylmethyl)-1,3-dioxolan-4-ylmethylthio]benzenamine dihydrochloride; mp. 194.9° C.;
cis-S-[2-(2,4-dichlorophenyl)-2-(1H-imidazol-1-ylmethyl)-1,3-dioxolan-4-ylmethyl]ethanethioate; mp. 86.7° C.; and cis-N-[4-[[2-(bromomethyl)-2-(2-chloro-4-methoxyphenyl)-1,3-dioxolan-4-yl]methylthio]phenyl]acetamide.

EXAMPLE XVI

A mixture of 15 parts of 3-methyl-4-nitrophenol, 12 parts of dimethylcarbamothioic chloride, 14 parts of potassium carbonate and 160 parts of 2-propanone is stirred and refluxed overnight. The reaction mixture is cooled and poured onto water. The product is filtered off, washed with water and dried, yielding 23.2 parts of O-(3-methyl-4-nitrophenyl)dimethylcarbamothioate.

Following the same procedure and using equivalent amounts of the appropriate starting materials there are also prepared:
O-(3-chloro-4-nitrophenyl)dimethylcarbamothioate;
O-(2-methyl-4-nitrophenyl)dimethylcarbamothioate;
O-(2-chloro-4-nitrophenyl)dimethylcarbamothioate;
O-(2-methoxy-4-nitrophenyl)dimethylcarbamothioate; and
O-(3-methoxy-4-nitrophenyl)dimethylcarbamothioate.

EXAMPLE XVII

252 Parts of tetrahydrothiophene 1,1-dioxide are distilled azeotropically to dry with benzene. The latter is evaporated and 20 parts of O-(3-methyl-4-nitrophenyl)-dimethylcarbamothioate are added to the residue. The whole is stirred for 30 minutes at 200° C. under nitrogen atmosphere. The reaction mixture is cooled and poured onto water. The product is filtered off, washed and dried, yielding 18.3 parts of S-(3-methyl-4-nitrophenyl)-dimethylcarbamothioate.

Following the same procedure and using equivalent amounts of the appropriate starting materials there are also prepared:
S-(3-chloro-4-nitrophenyl)dimethylcarbamothioate;
S-(2-methyl-4-nitrophenyl)dimethylcarbamothioate;
S-(2-chloro-4-nitrophenyl)dimethylcarbamothioate;
S-(2-methoxy-4-nitrophenyl)dimethylcarbamothioate; and
S-(3-methoxy-4-nitrophenyl)dimethylcarbamothioate.

EXAMPLE XVIII

A mixture of 16 parts of S-(3-methyl-4-nitrophenyl)-dimethylcarbamothioate and 240 parts of methanol, saturated with ammonia is hydrogenated at normal pressure and at room temperature with 3 parts of platinum-on-charcoal 5%. After the calculated amount of hydrogen is taken up, the catalyst is filtered off and the filtrate is evaporated. The residue is dissolved in dichloromethane. The solution is washed with water, dried, filtered and evaporated. The residue is triturated in 2,2'-oxybispropane. The product is filtered off and dried, yielding 11.1 parts of S-(4-amino-3-methylphenyl)dimethylcarbamothioate.

Following the same procedure and using equivalent amounts of the appropriate starting materials there are also prepared:
S-(4-amino-3-chlorophenyl)dimethylcarbamothioate;
S-(4-amino-2-methylphenyl)dimethylcarbamothioate;
S-(4-amino-2-chlorophenyl)dimethylcarbamothioate;
S-(4-amino-2-methoxyphenyl)dimethylcarbamothioate; and
S-(4-amino-3-methoxyphenyl)dimethylcarbamothioate.

EXAMPLE XIX

A mixture of 6.3 parts of S-(4-amino-3-methylphenyl)dimethylcarbamothioate, 2.4 parts of sodium hydroxide and 80 parts of methanol is stirred and refluxed for 5 hours. Then there are added 12 parts of cis-2-(2,4-dichlorophenyl)-2-(1H-imidazol-1-ylmethyl)-1,3-dioxolan-4-ylmethanol methanesulfonate (ester) and the whole is stirred and refluxed overnight. The reaction mixture is cooled and poured onto water. The product is extracted with dichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is converted into the hydrochloride salt in 2-propanol. The salt is filtered off and dried, yielding 12 parts of cis-4-[[2-(2,4-dichlorophenyl)-2-(1H-imidazol-1-ylmethyl)-1,3-dioxolan-4-yl]methylthio]-2-methylbenzenamine dihydrochloride.

In a similar manner there are also prepared starting from cis-2-(2,4-dichlorophenyl)-2-(1H-imidazol-1-ylmethyl)-1,3-dioxolan-4-ylmethanol methanesulfonate (ester):
cis-2-chloro-4-[[2-(2,4-dichlorophenyl)-2-(1H-imidazol-1-ylmethyl)-1,3-dioxolan-4-yl]methylthio]benzenamine dihydrochloride; mp. 202.1° C.;
cis-4-[[2-(2,4-dichlorophenyl)-2-(1H-imidazol-1-ylmethyl)-1,3-dioxolan-4-yl]methylthio]-3-methylbenzenamine dihydrochloride;
cis-3-chloro-4-[[2-(2,4-dichlorophenyl)-2-(1H-imidazol-1-ylmethyl)-1,3-dioxolan-4-yl]methylthio]benzenamine dihydrochloride;
cis-4-[[2-(2,4-dichlorophenyl)-2-(1H-imidazol-1-ylmethyl)-1,3-dioxolan-4-yl]methylthio]-3-methoxybenzenamine dihydrochloride; and
cis-4-[[2-(2,4-dichlorophenyl)-2-(1H-imidazol-1-ylmethyl)-1,3-dioxolan-4-yl]methylthio]-2-methoxybenzenamine dihydrochloride.

EXAMPLE XX

A mixture of 64 parts of cis-N-[4-[2-(2,4-dichlorophenyl)-2-(1H-1,2,4-triazol-1-ylmethyl)-1,3-dioxolan-4-ylmethylthio]phenyl]acetamide monohydrochloride, 10 parts of sodium hydroxide and 800 parts of 2-propanol is stirred and refluxed overnight. The reaction mixture is evaporated and the residue is taken up in water. The product is extracted with dichloromethane. The extract is washed with water, dried, filtered and evaporated. The residue is converted into the hydrochloride salt in 2-propanol. The salt is filtered off and dried, yielding 45.5 parts of cis-4-[2-(2,4-dichlorophenyl)-2-(1H-1,2,4-triazol-1-ylmethyl)-1,3-dioxolan-4-ylmethylthio]benzenamine monohydrochloride; mp. 218.1° C.

In a similar manner there are also prepared:
trans-4-[[2-(2,4-dichlorophenyl)-2-(1H-imidazol-1-ylmethyl)-1,3-dioxolan-4-yl]methylthio]benzenamine dihydrochloride; and
cis-4-[[2-(2-chloro-4-methoxyphenyl)-2-(1H-imidazol-1-ylmethyl)-1,3-dioxolan-4-yl]methylthio]benzenamine as a residue.

EXAMPLE XXI

To a stirred solution of 3.2 parts of carbonothioic dichloride in 150 parts of trichloromethane and 50 parts of crushed ice is added dropwise, during a 15 minutes-period, a solution of 8.7 parts of cis-4-[2-(2,4-dichlorophenyl)-2-(1H-imidazol-1-ylmethyl)-1,3-dioxolan-4-ylmethylthio]benzenamine in 38 parts of trichloromethane at 0° C. Upon completion, stirring is continued for 30 minutes at room temperature. Sodium hydrogen carbonate is added and the layers are separated. The organic phase is dried, filtered and evaporated. The residue is triturated in a mixture of 4-methyl-2-pentanone and 2,2'-oxybispropane. The product is filtered off and crystallized from 4-methyl-2-pentanone, yielding 5.4 parts of cis-1-[2-(2,4-dichlorophenyl)-4-[(4-isothiocyanatophenyl)thiomethyl]-1,3-dioxolan-2-ylmethyl]-1H-imidazole; mp. 149.8° C.

EXAMPLE XXII

A mixture of 20 parts of cis-1-[2-(2,4-dichlorophenyl)-4-[(4-nitrophenylmethyl)thiomethyl]-1,3-dioxolan-2-ylmethyl]-1H-imidazole and 400 parts of methanol, saturated with ammonia, is hydrogenated at normal pressure and at room temperature with 4 parts of platinum-on-charcoal catalyst 5%. After the calculated amount of hydrogen is taken up, the catalyst is filtered off and the filtrate is evaporated. The residue is purified by column-chromatography over silica gel using a mixture of trichloromethane, hexane and methanol (45:45:10 by volume) as eluent. The pure fractions are collected and the eluent is evaporated, yielding 12.5 parts of cis-4-[[2-(2,4-dichlorophenyl)-2-(1H-imidazol-1-ylmethyl)-1,3-dioxolan-4-ylmethyl]thiomethyl]benzenamine as a residue.

EXAMPLE XXIII

To a stirred mixture of 11.9 parts of thionyl chloride and 225 parts of trichloromethane are added portionwise 6.9 parts of cis-2-(2,4-dichlorophenyl)-2-(1H-imidazol-1-ylmethyl)-1,3-dioxolane-4-ethanol. Upon completion, the whole is heated to reflux and stirring is continued for 4 hours at reflux temperature. The reaction mixture is evaporated, the residue is taken up in methylbenzene and the latter is evaporated again. The residue is dissolved in dichloromethane. The solution is washed with a sodium hydrogen carbonate solution and with water, dried, filtered and evaporated. The residue is converted into the nitrate salt in 2,2'-oxybispropane. The salt is filtered off and dried, yielding 7.8 parts (91.8%) of cis-1-[[4-(2-chloroethyl)-2-(2,4-dichlorophenyl)-1,3-dioxolan-2-yl]methyl]-1H-imidazole mononitrate; mp. 160.5° C.

EXAMPLE XXIV

To a stirred and cooled mixture of 63.7 parts of 1,2,4-butanetriol and 64.1 parts of 1-(2,4-dichlorophenyl)-2-(1H-imidazol-1-yl)ethanone 4-methylbenzenesulfonate (1:1) are added dropwise 600 parts of methanesulfonic acid. Upon completion, stirring is continued over week-end at room temperature. The reaction mixture is poured onto a mixture of crushed ice and sodium hydroxide. The product is extracted with dichloromethane. The extract is dried, filtered and evaporated. The residue is purified by column-chromatography over silica gel using a mixture of trichloromethane and methanol (97:3 by volume) as eluent. The pure fractions are collected and the eluent is evaporated. The residue is crystallized from a mixture of methylbenzene and 2,2'-oxybispropane. The product is filtered off and recrystallized from methylbenzene, yielding 10.8 parts of cis-2-(2,4-dichlorophenyl)-2-(1H-imidazol-1-ylmethyl)-1,3-dioxolane-4-ethanol; mp. 106.5° C.

EXAMPLE XXV

To a stirred mixture of 3.9 parts of cis-S-[2-(2,4-dichlorophenyl)-2-(1H-imidazol-1-ylmethyl)-1,3-dioxolan-4-ylmethyl]ethanedioate and 75 parts of methanol is added dropwise a solution of 3.1 parts of potassium carbonate in 25 parts of water under nitrogen-atmosphere. Upon completion, stirring is continued for 1 hour at 40° C. while nitrogen is still introduced. Then there are added 3.1 parts of 1-(chloromethyl)-4-nitrobenzene and stirring is continued for 2 hours at 30°-40° C. The nitrogen-introduction is ceased and the reaction mixture is cooled. Then dichloromethane is added. The whole is washed with water, dried, filtered and evaporated. The residue is converted into the nitrate salt in 4-methyl-2-pentanone. The salt is crystallized from 4-methyl-2-pentanone, yielding 3 parts of cis-1-[2-(2,4-dichlorophenyl)-4-[(4-nitrophenylmethyl)thiomethyl]-1,3-dioxolan-2-ylmethyl]-1H-imidazole mononitrate; mp. 162.8° C.

EXAMPLE XXVI

A mixture of 36.8 parts of 1,2,3-propanetriol, 23 parts of 1-(4-bromophenyl)-2-(1H-imidazol-1-yl)ethanone and 330 parts of methanesulfonic acid is stirred for 4 hours at 40° C. The reaction mixture is cooled and allowed to stand overnight at room temperature. It is added dropwise to a dilute sodium hydroxide solution and the product is extracted with trichloromethane. The extract is washed with water, dried, filtered and evaporated, yielding 15 parts of (cis+trans)-2-(4-bromophenyl)-2-(1H-imidazol-1-ylmethyl)-1,3-dioxolane-4-methanol as a residue.

B. PREPARATION OF FINAL COMPOUNDS

EXAMPLE XXVII

To a stirred mixture of 25 parts of N-(4-mercaptophenyl)acetamide and 200 parts of dimethylsulfoxide are added 7.5 parts of sodium hydride dispersion 50% and stirring is continued till gas-evolution has ceased. Then there are added 67.5 parts of cis-[2-(2,4-dichlorophenyl)-2-(1H-imidazol-1-ylmethyl)-1,3-dioxolan-4-ylmethyl]methanesulfonate and the whole is stirred first for 3 hours at 60° C. and further overnight at room temperature. The reaction mixture is poured onto water and the product is extracted three times with dichloromethane. The combined extracts are washed three times with water, dried, filtered and evaporated. The residue is purified by column-chromatography over silica gel using a mixture of trichloromethane, methanol, and methanol saturated with ammonia (95:4:1 by volume) as eluent. The pure fractions are collected and the eluent is evaporated. The residue is converted into the hydrochloride salt in 2-propanone. The salt is filtered off and dried, yielding 43 parts of cis-N-[4-[2-(2,4-dichlorophenyl)-2-(1H-imidazol-1-ylmethyl)-1,3-dioxolan-4-ylmethylthio]phenyl]acetamide monohydrochloride; mp. 186.2° C.

EXAMPLE XXVIII

A mixture of 2 parts of ethyl(4-mercaptophenyl)carbamate, 4 parts of cis-2-(2,4-dichlorophenyl)-2-(2-methyl-1H-imidazol-1-ylmethyl)-1,3-dioxolane-4-methanol methanesulfonate (ester), 1.4 parts of potassium carbonate and 32 parts of 2-propanone is stirred and refluxed for 4 hours. Stirring is continued overnight at room temperature. The reaction mixture is poured onto water and the product is extracted with dichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is triturated in a mixture of 2,2'-oxybispropane and 4-methyl-2-pentanone. The product is filtered off and dried, yielding 3.9 parts of cis-ethyl[4-[[2-(2,4-dichlorophenyl)-2-(2-methyl-1H-imidazol-1-ylmethyl)-1,3-dioxolan-4-yl]methylthio]phenyl]carbamate; mp. 119.7° C.

Following the same procedure and using equivalent amounts of the appropriate starting materials there are also prepared:

cis-ethyl[4-[2-(2-chloro-4-nitrophenyl)-2-(1H-imidazol-1-ylmethyl)-1,3-dioxolan-4-ylmethylthio]phenyl]carbamate; mp. 207.5° C.;

cis-N-[4-[[2-(2,4-dichlorophenyl)-2-[(2-ethyl-1H-imidazol-1-yl)methyl]-1,3-dioxolan-4-yl]methylthio]phenyl]acetamide; mp. 171.5° C.;

cis-N-[4-[[2-(2,4-dichlorophenyl)-2-[(2-methyl-1H-imidazol-1-yl)methyl]-1,3-dioxolan-4-yl]methylthio]phenyl]acetamide; mp. 173.7° C.; and cis-N-[4-[2-(2,4-dichlorophenyl)-2-(1H-1,2,4-triazol-1-ylmethyl)-1,3-dioxolan-4-ylmethylthio]phenyl]acetamide monohydrochloride.

EXAMPLE XXIX

To a stirred mixture of 5 parts of cis-4-[2-(2,4-dichlorophenyl)-2-(1H-imidazol-1-ylmethyl)-1,3-dioxolan-4-ylmethylthio]benzenamine dihydrochloride, 4.3 parts of potassium carbonate, 50 parts of water and 130 parts of dichloromethane are added dropwise 2 parts of ethyl carbonochloridate. Upon completion, stirring is continued for 2 hours at room temperature. The reaction mixture is poured onto water and the product is extracted three times with dichloromethane. The combined extracts are washed with water, dried, filtered and evaporated. The residue is triturated in 2,2'-oxybispropane. The product is filtered off and dried, yielding 4.6 parts of cis-ethyl[4-[2-(2,4-dichlorophenyl)-2-(1H-imidazol-1-ylmethyl)-1,3-dioxolan-4-ylmethylthio]phenyl]carbamate; mp. 156.2° C.

Following the same procedure and using equivalent amounts of the appropriate starting materials there are also prepared:

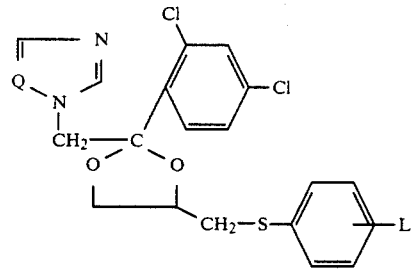

| Q | L | stereochem. isomeric form | base/salt | mp. °C. |
|---|---|---|---|---|
| CH | 4-NH—COO—CH$_2$—C$_6$H$_5$ | cis | base | 93.0 |
| CH | 4-NH—COO—C$_2$H$_5$ | cis | HCl.H$_2$O | 152.8 |
| CH | 4-NH—COO—CH$_2$CH(CH$_3$)$_2$ | cis | base | 121.5 |
| CH | 4-NH—COOn.C$_5$H$_{11}$ | cis | base | 131.2 |
| CH | 4-NH—COOn.C$_3$H$_7$ | cis | base | 138.1 |
| CH | 4-NH—COOi.C$_3$H$_7$ | cis | base | 139.6 |
| CH | 4-NH—COOc.C$_6$H$_{11}$ | cis | base | 162.7 |
| CH | 4-NH—COOn.C$_4$H$_9$ | cis | base | 123.5 |
| CH | 4-NH—COOc.C$_5$H$_9$ | cis | base | 129.2 |
| CH | 3-NH—COO—CH$_3$ | cis | base | 157.8 |
| CH | 3-NH—COO—C$_2$H$_5$ | cis | base | 121.9 |
| CH | 4-NH—COO—n.C$_7$H$_{15}$ | cis | base | 112.6 |
| CH | 4-NH—COO—n.C$_9$H$_{19}$ | cis | base | 118.4 |
| CH | 4-NH—COO—n.C$_8$H$_{17}$ | cis | base | 113.8 |
| CH | 4-NH—COO—CH$_2$CH(CH$_3$)C$_2$H$_5$ | cis | base | 90.4 |
| CH | 4-NH—COOCH$_2$CH$_2$OCH(CH$_3$)$_2$ | cis | 2 H$_2$O | 78.0 |
| CH | 4-NH—COOCH(CH$_3$)C$_2$H$_5$ | cis | base | 97.0 |
| CH | 4-NH—COO n.C$_6$H$_{13}$ | cis | base | 114.8 |
| CH | 4-NH—COOCH$_2$—CH$_2$Cl | cis | base | 143.8 |
| CH | 4-NH—COOCH$_2$CCl$_3$ | cis | base | 140.6 |
| CH | 4-NH—COO(CH$_2$)$_3$—CH$_2$Cl | cis | base | 104.3 |
| CH | 4-NH—COO(CH$_2$)$_2$—O—C$_6$H$_5$ | cis | base | 140.2 |
| CH | 4-NH—COOCH$_2$CH=CH$_2$ | cis | base | 134.9 |
| CH | 4-NH—COOCH$_2$CH$_2$COOC$_2$H$_5$ | cis | base | 83.0 |
| CH | 4-NH—COOC$_2$H$_5$ | trans | base | 114.5 |
| CH | 4-NH—COOCH$_3$ | trans | base | 126.6 |
| CH | 4-NH—COOCH$_2$CH$_2$OCH$_3$ | cis | base | 102.7 |
| CH | 4-NH—COOCH$_2$CH$_2$OC$_2$H$_5$ | cis | base | 96.9 |
| CH | 4-NH—COOCH$_2$CH$_2$SC$_2$H$_5$ | cis | base | 109.8 |
| CH | 4-NH—COOCH$_2$CH$_2$C$_6$H$_5$ | cis | base | 116.4 |
| CH | 4-NH—COOCH$_2$CH$_2$COOCH$_3$ | cis | base | 99.2 |
| CH | 4-NH—COOCH$_2$COOC$_2$H$_5$ | cis | base | 131.2 |
| CH | 4-NH—COOCH$_2$CH$_2$SCH$_3$ | cis | base | 112.8 |
| CH | 4-NH—COOCH$_2$CH$_2$S—n.C$_3$H$_7$ | cis | base | 96.5 |
| N | 4-NH—COOC$_2$H$_5$ | cis | base | 104.8 |
| N | 4-NH—COOCH$_3$ | cis | HCl | 165.8 |
| N | 4-NH—COO—n.C$_3$H$_7$ | cis | base | 95.8 |
| N | 4-NH—COO—i.C$_3$H$_7$ | cis | base | 105.2 |

In a similar manner there are also prepared:

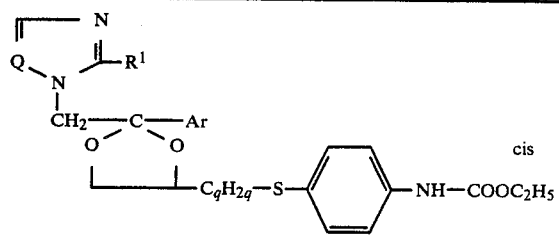

| Q | R$^1$ | q | Ar | base/salt | mp. in °C. |
|---|---|---|---|---|---|
| CH | C$_2$H$_5$ | 1 | 2,4-Cl$_2$—C$_6$H$_3$ | base | 129.2 |
| CH | H | 2 | 2,4-Cl$_2$—C$_6$H$_3$ | 1½ (COOH)$_2$ | 128.2 |
| N  | H | 2 | 2,4-Cl$_2$—C$_6$H$_3$ | (COOH)$_2$ | 127.4 |
| CH | H | 1 | 2-Cl,4-F—C$_6$H$_3$ | base | 143.1 |
| CH | H | 1 | 4-Cl—C$_6$H$_4$ | base | 143.7 |
| CH | H | 1 | 2-Cl,4-Br—C$_6$H$_3$ | base | 166.3 |
| CH | H | 1 | 4-Br—C$_6$H$_4$ | base | 147.6 |

EXAMPLE XXX

To a stirred mixture of 5 parts of cis-4-[2-(2,4-dichlorophenyl)-2-(1H-imidazol-1-ylmethyl)-1,3-dioxolan-4-ylmethylthio]benzenamine, 10 parts of pyridine and 78 parts of dichloromethane is added dropwise a solution of 1.5 parts of methyl carbonochloridate in 52 parts of dichloromethane. Upon completion, stirring is continued for 3 hours at room temperature. The reaction mixture is poured onto water and the product is extracted three times with dichloromethane. The combined extracts are washed four times with water, dried, filtered and evaporated. The residue is triturated in 2,2'-oxybispropane. The product is filtered off and crystallized from 2-propanol, yielding 2.7 parts of methyl cis-[4-[2-(2,4-dichlorophenyl)-2-(1H-imidazol-1-ylmethyl)-1,3-dioxolan-4-ylmethylthio]phenyl]carbamate; mp. 136.5° C.

Following the same procedure and using equivalent amounts of the appropriate starting materials there are also prepared:

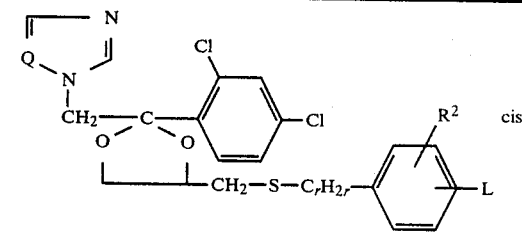

| Q | R$^2$ | L | r | base/salt | mp. °C. |
|---|---|---|---|---|---|
| CH | H | 2-NH—COOCH$_3$ | 0 | base | 120.1 |
| CH | H | 2-NH—COOC$_2$H$_5$ | 0 | base | 107.6 |
| CH | 3-CH$_3$ | 4-NH—COOCH$_3$ | 0 | base | 122.7 |
| CH | 3-Cl | 4-NH—COOCH$_3$ | 0 | base | 118.4 |
| CH | 3-Cl | 4-NH—COOC$_2$H$_5$ | 0 | base | 107.9 |
| CH | 3-CH$_3$ | 4-NH—COOC$_2$H$_5$ | 0 | base | 131.1 |
| CH | 2-CH$_3$ | 4-NH—COOCH$_3$ | 0 | base | 140.4 |
| CH | 2-CH$_3$ | 4-NH—COOC$_2$H$_5$ | 0 | base | 128.0 |
| CH | 2-Cl | 4-NH—COOCH$_3$ | 0 | base | 150.6 |
| CH | 2-Cl | 4-NH—COOC$_2$H$_5$ | 0 | base | 141.4 |
| CH | 2-OCH$_3$ | 4-NH—COOC$_2$H$_5$ | 0 | base | 148.0 |
| CH | 3-OCH$_3$ | 4-NH—COOCH$_3$ | 0 | base | 119.0 |
| CH | 2-OCH$_3$ | 4-NH—COOCH$_3$ | 0 | base | 157.8 |
| CH | 3-OCH$_3$ | 4-NH—COOC$_2$H$_5$ | 0 | base | 110.7 |
| CH | H | 4-NH—COOCH$_3$ | 1 | 3(COOH)$_2$·3H$_2$O | 113.6 |
| CH | H | 4-NH—COOC$_2$H$_5$ | 1 | 4(COOH)$_2$·4H$_2$O | 80.6 |

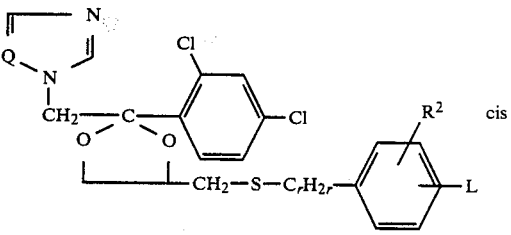

| Q | R$^2$ | L | r | base/salt | mp. °C. |
|---|---|---|---|---|---|

In a similar manner there is also prepared:
ethyl cis-[4-[[2-(2-chloro-4-methoxyphenyl)-2-(1H-imidazol-1-ylmethyl)-1,3-dioxolan-4-yl]methylthio]phenyl]carbamate; mp. 149.0° C.

EXAMPLE XXXI

To a stirred solution of 14.2 parts of cis-4-[2-(2,4-dichlorophenyl)-2-(1H-imidazol-1-ylmethyl)-1,3-dioxolan-4-ylmethylthio]benzeneamine and 10 parts of sodium hydrogen carbonate in 45 parts of benzene and 200 parts of water are added dropwise, during a 15 minutes-period, 7 parts of phenyl carbonochloridate. Upon completion, stirring is continued for 30 minutes at room temperature. The organic phase is separated and evaporated at 30° C. The residue is triturated in 4-methyl-2-pentanone. The product is filtered off and dried, yielding 17 parts (94%) of phenyl cis-[4-[2-(2,4-dichlorophenyl)-2-(1H-imidazol-1-ylmethyl)-1,3-dioxolan-4-ylmethylthio]phenyl]carbamate.

EXAMPLE XXXII

A mixture of 1.6 parts of propanoic acid anhydride, 5 parts of cis-4-[2-(2,4-dichlorophenyl)-2-(1H-imidazol-1-ylmethyl)-1,3-dioxolan-4-ylmethylthio]benzenamine, 4.3 parts of potassium carbonate, 50 parts of water and 130 parts of dichloromethane is stirred and refluxed for 2 days. The reaction mixture is poured onto water and the product is extracted with dichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is converted into the ethanedioate salt in 4-methyl-2-pentanone. The salt is filtered off and crystallized from acetonitrile. The product is filtered off and recrystallized from 2-propanol, yielding 3.1 parts of cis-N-[4-[2-(2,4-dichlorophenyl)-2-(1H-imidazol-1-ylmethyl)-1,3-dioxolan-4-ylmethylthio]phenyl]propanamide ethanedioate (1:1); mp. 159° C.

In a similar manner there is also prepared:
cis-N-[4-[2-(2,4-dichlorophenyl)-2-(1H-1,2,4-triazoi-1-ylmethyl)-1,3-dioxolan-4-ylmethylthio]phenyl]propanamide; mp. 123.2° C.

EXAMPLE XXXIII

To a stirred mixture of 4.3 parts of cis-4-[2-(2,4-dichlorophenyl)-2-(1H-imidazol-1-ylmethyl)-1,3-dioxolan-4-ylmethylthio]benzenamine, 80 parts of 1-butanol and 50 parts of water are added 4.4 parts of bis(1,1-dimethylethyl)dicarbonate and the whole is stirred for 2 days at 60° C. The reaction mixture is poured onto water and the product is extracted with dichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is triturated in a mixture of 2,2'-oxybispropane and 4-methyl-2-pentanone. The product is filtered off and dried, yielding 1.7 parts of 1,1-dimethylethyl cis-[4-[[2-(2,4-dichlorophenyl)-2-(1H-imidazol-1-ylmethyl)-1,3-dioxolan-4-yl]methylthio]phenyl]carbamate; mp. 124° C.

EXAMPLE XXXIV

A mixture of 120 parts of formic acid and 4.4 parts of cis-4-[2-(2,4-dichlorophenyl)-2-(1H-imidazol-1-ylmethyl)-1,3-dioxolan-4-ylmethylthio]benzenamine is stirred and refluxed for 2 days. The reaction mixture is cooled and evaporated. The residue is taken up in water, alkalized with sodium hydrogen carbonate and the product is extracted with dichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is triturated in 2,2'-oxybispropane. The product is filtered off and crystallized from methylbenzene, yielding 3 parts of cis-N-[4-[2-(2,4-dichlorophenyl)-2-(1H-imidazol-1-ylmethyl)-1,3-dioxolan-4-ylmethylthio]phenyl]formamide; mp. 113.8° C.

In a similar manner there is also prepared:
cis-N-[4-[2-(2,4-dichorophenyl)-2-(1H-1,2,4-triazol-1-ylmethyl)-1,3-dioxolan-4-ylmethylthio]phenyl]formamide; mp. 122.4° C.

EXAMPLE XXXV

A mixture of 1 part of potassium cyanate, 5 parts of cis-4-[2-(2,4-dichlorophenyl)-2-(1H-imidazol-1-ylmethyl)-1,3-dioxolan-4-ylmethylthio]benzenamide, 100 parts of water and 20 parts of acetic acid is stirred overnight at room temperature. The reaction mixture is poured onto water and the whole is alkalized with sodium hydrogen carbonate. The product is extracted three times with trichloromethane. The combined extracts are washed with water, dried, filtered and evaporated. The residue is triturated in 2,2'-oxybispropane. The product is filtered off and purified by column-chromatography over silica gel using a mixture of trichloromethane and methanol (90:10 by volume) as eluent. The pure fractions are collected and the eluent is evaporated. The residue is triturated in 2,2'-oxybispropane. The product is filtered off and dried, yielding 3.4 parts of cis-N-[4-[2-(2,4-dichlorophenyl)-2-(1H-imidazole-1-ylmethyl)-1,3-dioxolan-4-ylmethylthio]phenyl]urea hemihydrate; mp. 139.4° C.

EXAMPLE XXXVI

A mixture of 0.7 parts of isocyanatomethane, 5 parts of cis-4-[2-(2,4-dichlorophenyl)-2-(1H-imidazol-1-ylmethyl)-1,3-dioxolan-4-ylmethylthio]benzenamine, 3.2 parts of N,N-diethylethanamine and 104 parts of dichloromethane is stirred over week-end at room temperature. The reaction mixture is poured onto water and the product is extracted with dichloromethane. The extract is washed with water, dried, filtered and evaporated. The residue is purified twice by column-chromatography over silica gel using first a mixture of trichloromethane and methanol (98:2 by volume) and the a mixture of hexane, trichloromethane and methanol (45:45:10 by volume) as eluent. The pure fractions are collected and the eluent is evaporated. The residue is converted into the hydrochloride salt in 4-methyl-2-pentanone and 2-propanol, yielding 1.7 parts of cis-N-[4-[2-(2,4-dichlorophenyl)-2-(1H-imidazol-1-ylmethyl)-1,3-dioxolan-4-ylmethylthio]phenyl]-N'-methylurea monohydrochloride; mp. 175° C.

In a similar manner there is also prepared:
cis-N-[4-[2-(2,4-dichlorophenyl)-2-(1H-1,2,4-triazol-1-ylmethyl)-1,3-dioxolan-4-ylmethylthio]phenyl]-N'-methylurea; mp. 115.5° C.

EXAMPLE XXXVII

A mixture of 1 part of isothiocyanatomethane, 5 parts of cis-4-[2-(2,4-dichlorophenyl)-2-(1H-imidazol-1-ylmethyl)-1,3-dioxolan-4-ylmethylthio]benzenamine dihydrochloride, 3.2 parts of N,N-diethylethanamine and 100 parts of 1,4-dioxane is stirred and refluxed for 2 hours. The reaction mixture is cooled, poured onto water and extracted three times with benzene. The combined extracts are washed with water, dried, filtered and evaporated. The residue is purified twice by column-chromatography over silica gel using first a mixture of trichloromethane and methanol (98:2 by volume) and then a mixture of trichloromethane, hexane and methanol (47.5:47.5:5 by volume) as eluent. The pure fractions are collected and the eluent is evaporated. The residue is triturated in 2,2'-oxybispropane. The product is filtered off and dried, yielding 2.3 parts of cis-N-[4-[2-(2,4-dichlorophenyl)-2-(1H-imidazol-1-ylmethyl)-1,3-dioxolan-4-ylmethylthio]phenyl]-N'-methylthiourea; mp. 144° C.

EXAMPLE XXXVIII

To a stirred solution of 5 parts of cis-1-[2-(2,4-dichlorophenyl)-4-[(4-isothiocyanatophenyl)thiomethyl]-1,3-dioxolan-2-ylmethyl]-1H-imidazole in 104 parts of dichloromethane are added 9 parts of ammonium hydroxide and stirring is continued overnight at room temperature. The reaction mixture is poured onto water and the product is extracted with dichloromethane. The extract is washed with water, dried, filtered and evaporated. The residue is purified by column-chromatography over silica gel using a mixture of trichloromethane and methanol (96:4 by volume) as eluent. The pure fractions are collected and the eluent is evaporated. The residue is triturated in a mixture of 2,2'-oxybispropane and 4-methyl-2-pentanone. The product is filtered off and crystallized from ethanol, yielding 1.7 parts of cis-N-[4-[2-(2,4-dichlorophenyl)-2-(1H-imidazol-1-ylmethyl)-1,3-dioxolan-4-ylmethylthio]phenyl]thiourea; mp. 191.3° C.

EXAMPLE XXXIX

To a stirred mixture of 5 parts of cis-1-[2-(2,4-dichlorophenyl)-4-[(4-isothiocyanatophenyl)thiomethyl]-1,3-dioxolan-2-ylmethyl]-1H-imidazole and 130 parts of dichloromethane are added dropwise 1.8 parts of N-ethylethanamine. Upon completion, stirring is continued for 3 hours at room temperature. The reaction mixture is poured onto water and the product is extracted with dichloromethane. The extract is washed with water, dried, filtered and evaporated. The residue is purified twice by column-chromatography over silica gel using first a mixture of trichloromethane and methanol (98:2 by volume) and then a mixture of methylbenzene and methanol (95:5 by volume) as eluent. The pure fractions are collected an the eluent is evaporated. The residue is triturated in a mixture of 2,2'-oxybispropane and 4-methyl-2-pentanone. The product is filtered off and crystallized from ethyl acetate. It is filtered off again and dried in vacuo for 2 days at 80° C., yielding 1.2 parts of cis-N-[4-[2-(2,4-dichlorophenyl)-2-(1H-imidazol-1-ylmethyl)-1,3-dioxolan-4-ylmethylthio]phenyl]-N',N'-diethylthiourea; mp. 123.5° C.

EXAMPLE XL

A mixture of 4.5 parts of hydrazine hydrate, 4.3 parts of cis-1-[2-(2,4-dichlorophenyl)-4-[(4-isothiocyanatophenyl)thiomethyl]-1,3-dioxolan-2-ylmethyl]-1H-imidazole and 80 parts of methanol is stirred and refluxed for 30 minutes. The reaction mixture is evaporated and the residue is dissolved in dichloromethane. The solution is washed twice with water, dried, filtered and evaporated. The residue is triturated in a mixture of 2-propanol and 2,2'-oxybispropane. The product is filtered off and crystallized from 2-propanol, yielding 4.7 parts (100%) of cis-N-[4-[2-(2,4-dichlorophenyl)-2-(1H-imidazol-1-ylmethyl)-1,3-dioxolan-4-ylmethylthio]phenyl]hydrazinecarbothioamide; mp. 138.9° C.

EXAMPLE XLI

To a stirred sodium ethoxide solution, prepared starting from 0.5 parts of sodium in 80 parts of ethanol, are added 5 parts of cis-1-[2-(2,4-dichlorophenyl)-4-[(4-isothiocyanatophenyl)thiomethyl]-1,3-dioxolan-2-ylmethyl]-1H-imidazole and the whole is stirred and refluxed for 6 hours. Stirring is continued overnight at room temperature. The reaction mixture is evaporated and the residue is taken up in water. The product is extracted with dichloromethane. The extract is washed with water, dried, filtered and evaporated. The residue is purified twice by column-chromatography over silica gel using a mixture of trichloromethane and methanol (98:2 by volume) as eluent. The pure fractions are collected and the eluent is evaporated. The residue is triturated in a mixture of petroleumether and 4-methyl-2-pentanone. The product is filtered off and dried, yielding 2.2 parts of cis-O-ethyl[4-[[2-(2,4-dichlorophenyl)-2-(1H-imidazol-1-ylmethyl)-1,3-dioxolan-4-yl]methylthio]phenyl]carbamate; mp. 132.5° C.

In a similar manner there is also prepared:
cis-O-methyl[4-[[2-(2,4-dichlorophenyl)-2-(1H-imidazol-1-ylmethyl)-1,3-dioxolan-4-yl]methylthio]phenyl]carbamothioate; mp. 135.8° C.

EXAMPLE XLII

A mixture of 50 parts of hydrazine hydrate, 72 parts of cis-phenyl[4-[2-(2,4-dichlorophenyl)-2-(1H-imidazol-1-ylmethyl)-1,3-dioxolan-4-ylmethylthio]phenyl]carbamate and 300 parts of 1,4-dioxane is stirred and refluxed for 5 hours. The reaction mixture is evaporated and water is added to the residue. The precipitated product is filtered off and dried, yielding 51 parts (79%) of cis-N-[4-[2-(2,4-dichlorophenyl)-2-(1H-imidazol-1-ylmethyl)-1,3-dioxolan-4-ylmethylthio]phenyl]hydrazinecarboxamide.

EXAMPLE XLIII

To a stirred mixture of 5 parts of cis-methyl[4-[2-(2,4-dichlorophenyl)-2-(1H-imidazol-1-ylmethyl)-1,3-dioxolan-4-ylmethylthio]phenyl]carbamate, 90 parts of benzene and 45 parts of N,N-dimethylformamide are added portionwise 0.5 parts of sodium hydride dispersion 50%. Upon completion, stirring at room temperature is continued till gas evolution has ceased. Then there is added 1 part of dimethylsulfate. The whole is stirred first for 3 hours at 50° C. and then overnight at room temperature. The reaction mixture is poured onto water and the product is extracted with benzene. The extract is dried, filtered and evaporated. The residue is purified twice by column-chromatography over silica gel using first a mixture of trichloromethane and methanol (98:2 by volume) and then a mixture of trichloromethane and methanol (97:3 by volume) as eluent. The pure fractions are collected and the eluent is evaporated. The residue is converted into the ethanedioate salt in 4-methyl-2-pentanone. The salt is filtered off and crystallized from 4-methyl-2-pentanone, yielding 1.6 parts of cis-methyl[4-[[2-(2,4-dichlorophenyl)-2-(1H-imidazol-1-ylmethyl)-1,3-dioxolan-4-yl]methylthio]phenyl]methylcarbamate ethanedioate (1:2); mp. 157.4° C.

In a similar manner there is also prepared:
cis-ethyl N-[4-[[2-(2,4-dichlorophenyl)-2-(1H-imidazol-1-ylmethyl)-1,3-dioxolan-4-yl]methylthio]phenyl]-N-methylcarbamate ethanedioate (1:2); mp. 130.5° C.

EXAMPLE XLIV

To a stirred mixture of 5 parts of cis-methyl[4-[2-(2,4-dichlorophenyl)-2-(1H-imidazol-1-ylmethyl)-1,3-dioxolan-4-ylmethylthio]phenyl]carbamate in 55 parts of N,N-dimethylformamide and 80 parts of benzene are added 0.5 parts of sodium hydride dispersion 50% and the whole is further stirred till gas-evolution has ceased. Then there are added 1.1 parts of bromoethane and the mixture is further stirred for 2 hours at 50° C. The reaction mixture is poured onto water and the product is extracted with benzene. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is converted into the ethanedioate salt in 4-methyl-2-pentanone. The crude salt is filtered off and crystallized from 4-methyl-2pentanone, yielding 4.8 parts of cis-methyl[4-[[2-(2,4-dichlorophenyl)-2-(1H-imidazol-1-ylmethyl)-1,3-dioxolan-4-yl]methylthio]phenyl]ethylcarbamate ethanedioate (2:7); mp. 127° C.

In a similar manner there is also prepared:
cis-methyl[4-[[2-(2,4-dichlorophenyl)-2-(1H-imidazol-1-ylmethyl)-1,3-dioxolan-4-yl]methylthio]phenyl]ethylcarbamate ethanedioate (2:3); mp. 138° C.

EXAMPLE XLV

A mixture of 3.5 parts of 1H-imidazole, 5 parts of trans-N-[4-[2-(bromomethyl)-2-(2,4-dichlorophenyl)-1,3-dioxolan-4-ylmethylthio]phenyl]acetamide and 90 parts of N,N-dimethylacetamide is stirred and refluxed for 24 hours. Stirring is continued over week-end at room temperature. The reaction mixture is poured onto water and the product is extracted with dichloromethane. The extract is washed with water, dried, filtered and evaporated. The residue is purified by column-chromatography over silica gel using a mixture of trichloromethane and methanol (98:2 by volume) as eluent. The pure fractions are collected and the eluent is evaporated. The residue is triturated in a mixture of petroleumether and 4-methyl-2-pentanone. The product is filtered off and dried, yielding 1.9 parts of trans-N-[4-[[2-(2,4-dichlorophenyl)-2-(1H-imidazol-1-ylmethyl)-1,3-dioxolan-4-yl]methylthio]phenyl]acetamide; mp. 117.9° C.

In a similar manner there is also prepared:
cis-N-[4-[[2-(2-chloro-4-methoxyphenyl)-2-(1H-imidazol-1-ylmethyl)-1,3-dioxolan-4-yl]methylthio]phenyl]acetamide as a residue.

EXAMPLE XLVI 2.8 Parts of cis-N-[4-[2-(2,4-dichlorophenyl)-2-(1H-1,2,4-triazol-1-ylmethyl)-1,3-dioxolan-4-ylmethylthio]phenyl]acetamide monohydrochloride are purified by column-chromatography over silica gel using a mixture of trichloromethane and methanol (97:3 by volume) as eluent. The pure fractions are collected and the eluent is evaporated, yielding 1.2 parts of cis-N-[4-[2-(2,4-dichlorophenyl)-2-(1H-1,2,4-triazol-1-ylmethyl)-1,3-dioxolan-4-ylmethylthio]phenyl]acetamide; mp. 155.2° C.

EXAMPLE XLVII

To a stirred and cooled (ice-bath) solution of 5 parts of methyl cis-[4-[2-(2,4-dichlorophenyl)-2-(1H-imidazol-1-ylmethyl)-1,3-dioxolan-4-ylmethylthio]phenyl]carbamate in 80 parts of methanol and 40 parts of acetonitrile is added dropwise a solution of 2.3 parts of sodium iodate in 25 parts of water. Upon completion, stirring is continued first overnight at room temperature and further for 3 days at reflux. The reaction mixture is evaporated and the residue is taken up in water. The product is extracted with trichloromethane. The extract is washed with water, dried, filtered and evaporated. The residue is purified twice by column-chromatography over silica gel using first a mixture of trichloromethane and methanol (98:2 by volume) and then a mixture of trichloromethane and methanol (96:4 by volume) as eluent. The pure fractions are collected and the eluent is evaporated. The residue is triturated in a mixture of 2,2'-oxybispropane and 4-methyl-2-pentanone. The product is filtered off and dried, yielding 2 parts of methyl cis-[4-[[2-(2,4-dichlorophenyl)-2-(1H-imidazol-1-ylmethyl)-1,3-dioxolan-4-yl]methylsulfinyl]phenyl]carbamate; mp. 208.9° C.

EXAMPLE XLVIII

To a stirred solution of 5 parts of ethyl cis[4-[2-(2,4-dichlorophenyl)-2-(1H-imidazol-1-ylmethyl)-1,3-dioxolan-4-ylmethylthio]phenyl]carbamate in 50 parts of acetic acid are added 5 parts of hydrogen peroxide solution 30%. Stirring is continued at reflux for 15 minutes. The reaction mixture is cooled and poured onto water. The whole is neutralized with sodium hydrogen carbonate. The product is extracted with trichloromethane. The extract is dried, filtered and evaporated. The residue is triturated in a mixture of 2,2'-oxybispropane and 4-methyl-2-pentanone. The product is filtered off and crystallized from 4-methyl-2-pentanone, yielding 3.2 parts of ethyl cis-[4-[[2-(2,4-dichlorophenyl)-2-(1H-imidazol-1-ylmethyl)-1,3-dioxolan-4-yl]methylsulfonyl]phenyl]carbamate; mp. 195.7° C.

In a similar manner there is also prepared:
methyl cis-[4-[[2-(2,4-dichlorophenyl)-2-(1H-imidazol-1-ylmethyl)-1,3-dioxolan-4-yl]methylsulfonyl]phenyl]carbamate; mp. 194.7° C.

What is claimed is:

1. A chemical compound selected from the group consisting of a pharmaceutically acceptable acid addition salt and a stereochemically isomeric form thereof, wherein Q is a member selected from the group consisting of CH and N;

$R^1$ is a member selected from the group consisting of hydrogen and lower alkyl;

Ar is aryl;

p is 0 or the integer 1 or 2;

q is the integer 1, 2 or 3;

r is 0 or the integer 1 or 2;

$R^2$ is a member selected from the group consisting of hydrogen, lower alkyl, lower alkyloxy and halo;

$R^3$ is a member selected from the group consisting of hydrogen, lower alkyl and aryllower alkyl;

X is a member selected from the group consisting of O and S;

Y is a member selected from the group consisting of O, S and $NR^5$, wherein $R^5$ is a member selected from the group consisting of hydrogen and lower alkyl;

m is 0 or the integer 1; and $R^4$ is a member selected from the group consisting of hydrogen, alkyl, mono-, di- and trihalolower alkyl, lower alkenyl, lower alkynyl, cycloalkyl, hydroxylower alkyl, lower alkoxy-lower alkyl, aryloxylower alkyl, aryllower aklyloxylower alkyl, mercaptolower alkyl, lower alkylthioether alkyl, arylthiolower alkyl, aryllower alkylthiolower alkyl, lower alkylcarbonyloxylower alkyl, arylcarbonyloxylower alkyl, aryllower alkylcarbonyloxylower alkyl, aryl, aryllower alkyl, lower alkyloxycarbonyllower alkyl, amino, and mono- and di(lower alkyl)amino; provided that Y is a radical $NR^5$ when m is 1 and $R^4$ is hydrogen, amino or amino-or di(lower alkyl)amino;

wherein aryl is a phenyl group which is optionally substituted with 1 to 3 substituents each independently selected from the group consisting of halo, lower alkyl, lower alkyloxy and nitro; alkyl is a hydrocarbon of from one to ten carbon atoms; and cycloalkyl is cyclopropyl, cyclobutyl, cyclopentyl, or cyclohexyl.

2. A chemical compound according to claim 1 wherein $R^1$ is hydrogen.

3. A chemical compound according to claim 1 wherein $R^1$ is hydrogen and Q is CH.

4. A chemical compound according to claim 1 wherein $R^1$ is hydrogen, Q is CH and r is 0.

5. A chemical compound according to claim 1 wherein $R^1$ is hydrogen, Q is CH, r is 0 and the $$-N(R^3)-\underset{X}{\overset{\|}{C}}-(Y)_m-R^4$$

group is attached at the 4-position of the phenyl ring.

6. A chemical compound selected from the group consisting of ethyl cis-[4-[2-(2,4-dichlorophenyl)-2-(1H-imidazol-1-ylmethyl)-1,3-dioxolan-4-ylmethyl]phenyl]-carbamate, a pharmaceutically acceptable acid-addition salt and a stereochemically isomeric form thereof.

7. A chemical compound according to claim 1 wherein Ar is dichlorophenyl, loweralkyloxyphenyl, or chlorophenyl additionally substituted with a loweralkyl or a loweralkyloxy substituent.

8. A chemical compound selected from the group consisting of ethyl cis-[4-[[2-(2-chloro-4-methoxyphenyl)-2-(1H-imidazol-1-ylmethyl)-1,3-dioxolan-4-yl]methylthio]phenyl]carbamate, a pharmaceutically acceptable acid-addition salt, and a stereochemically isomeric form thereof.

9. A chemical compound according to claim 1 wherein $R^1$ is hydrogen, Q is CH, r is 0, Y is a member selected from the group consisting of O and S, and $R^4$ is a member selected from the group consisting of alkyl and aryl.

10. A chemical compound according to claim 9 wherein Ar is a phenyl group substituted with 1 to 3 halo substituents.

11. A chemical compound according to claim 10 wherein q is 1, p is 0, $R^2$ and $R^3$ are hydrogen, and m is 1.

12. A chemical compound according to claim 11 wherein Ar is 2,4-dichlorophenyl.

* * * * *